US012329665B2

(12) United States Patent
Folan et al.

(10) Patent No.: US 12,329,665 B2
(45) Date of Patent: Jun. 17, 2025

(54) STENT WITH ANTI-MIGRATION FEATURES

(71) Applicant: BOSTON SCIENTIFIC SCIMED, INC., Maple Grove, MN (US)

(72) Inventors: Martyn G. Folan, Galway (IE); Gary Gilmartin, Foxford (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 907 days.

(21) Appl. No.: 17/487,937

(22) Filed: Sep. 28, 2021

(65) Prior Publication Data

US 2022/0096254 A1 Mar. 31, 2022

Related U.S. Application Data

(60) Provisional application No. 63/084,865, filed on Sep. 29, 2020.

(51) Int. Cl.
*A61F 2/90* (2013.01)
*D04B 1/22* (2006.01)
*D04B 21/20* (2006.01)

(52) U.S. Cl.
CPC ............... *A61F 2/90* (2013.01); *D04B 1/225* (2013.01); *D04B 21/205* (2013.01); *A61F 2220/0075* (2013.01); *A61F 2240/001* (2013.01); *D10B 2509/06* (2013.01)

(58) Field of Classification Search
CPC ............... A61F 2/90; A61F 2220/0075; A61F 2240/001; D04B 1/225; D04B 21/205; D10B 2509/06
See application file for complete search history.

(56) References Cited

U.S. PATENT DOCUMENTS

| 3,938,529 A | 2/1976 | Gibbons |
| 5,064,435 A | 11/1991 | Porter |
| 5,133,732 A | 7/1992 | Wiktor |
| 5,167,614 A | 12/1992 | Tessmann et al. |

(Continued)

FOREIGN PATENT DOCUMENTS

| CN | 201108514 Y | 9/2008 |
| CN | 201684049 U | 12/2010 |

(Continued)

OTHER PUBLICATIONS

International Search Report and Written Opinion dated Jan. 12, 2022 for International Application No. PCT/US2021/052436.

(Continued)

*Primary Examiner* — Suzette J Gherbi
(74) *Attorney, Agent, or Firm* — Seager, Tufte & Wickhem, LLP

(57) ABSTRACT

An illustrative stent may comprise an elongated tubular member having a first end and a second end and an intermediate region disposed therebetween. The elongated tubular member configured to move between a collapsed configuration and an expanded configuration. The elongated tubular member may comprise at least one twisted filament, such as a knitted filament having a plurality of twisted knit stitches with intermediate rung portions extending between adjacent twisted knit stitches and one or more anti-migration features formed in one or more intermediate rung portions.

17 Claims, 22 Drawing Sheets

(56) References Cited

U.S. PATENT DOCUMENTS

| | | | |
|---|---|---|---|
| 5,234,456 A | 8/1993 | Silvestrini | |
| 5,238,004 A | 8/1993 | Sahatjian et al. | |
| 5,242,462 A | 9/1993 | El-Nounou et al. | |
| 5,366,504 A | 11/1994 | Andersen et al. | |
| 5,383,927 A | 1/1995 | De Goicoechea et al. | |
| 5,607,464 A | 3/1997 | Trescony et al. | |
| 5,628,788 A | 5/1997 | Pinchuk | |
| 5,645,559 A | 7/1997 | Hachtman et al. | |
| 5,653,745 A | 8/1997 | Trescony et al. | |
| 5,662,713 A | 9/1997 | Andersen et al. | |
| 5,697,970 A | 12/1997 | Schmitt et al. | |
| 5,800,519 A | 9/1998 | Sandock | |
| 5,876,445 A | 3/1999 | Andersen et al. | |
| 5,984,965 A | 11/1999 | Knapp et al. | |
| 6,221,060 B1 | 4/2001 | Willard | |
| 6,240,978 B1 | 6/2001 | Gianotti | |
| 6,258,117 B1 | 7/2001 | Camrud et al. | |
| 6,264,689 B1 | 7/2001 | Colgan et al. | |
| 6,305,436 B1 | 10/2001 | Andersen et al. | |
| 6,358,275 B1 | 3/2002 | McIlroy et al. | |
| 6,416,537 B1 | 7/2002 | Martakos et al. | |
| 6,451,052 B1 | 9/2002 | Burmeister et al. | |
| 6,485,515 B2 | 11/2002 | Strecker | |
| 6,494,907 B1 | 12/2002 | Bulver | |
| 6,508,803 B1 | 1/2003 | Horikawa et al. | |
| 6,520,983 B1 | 2/2003 | Colgan et al. | |
| 6,540,773 B2 | 4/2003 | Dong | |
| 6,554,855 B1 | 4/2003 | Dong | |
| 6,652,577 B2 | 11/2003 | Gianotti | |
| 6,709,451 B1 | 3/2004 | Noble et al. | |
| 6,783,554 B2 | 8/2004 | Amara et al. | |
| 6,893,457 B2 | 5/2005 | Dong | |
| 6,939,372 B2 | 9/2005 | Dong | |
| 7,011,676 B2 | 3/2006 | Dong | |
| 7,169,139 B2 | 1/2007 | Teague et al. | |
| 7,195,646 B2 | 3/2007 | Nahleili | |
| 7,198,638 B2 | 4/2007 | Dong | |
| 7,338,530 B2 | 3/2008 | Carter et al. | |
| 7,364,587 B2 | 4/2008 | Dong et al. | |
| 7,594,928 B2 | 9/2009 | Headley, Jr. et al. | |
| D612,499 S | 3/2010 | Ondracek et al. | |
| 7,854,756 B2 | 12/2010 | Shaw | |
| 7,914,568 B2 | 3/2011 | Cully et al. | |
| 8,435,283 B2 | 5/2013 | Jordan et al. | |
| 8,435,285 B2 | 5/2013 | Shank et al. | |
| 8,454,675 B2 | 6/2013 | Houston et al. | |
| 8,753,407 B2 | 6/2014 | Nguyen | |
| 8,821,565 B2 | 9/2014 | Demetriades et al. | |
| 8,974,516 B2 | 3/2015 | Hyodoh et al. | |
| 9,265,635 B2 | 2/2016 | Walak | |
| 9,498,319 B2 | 11/2016 | Walak | |
| 9,839,508 B2 | 12/2017 | Walsh et al. | |
| 9,849,009 B2 | 12/2017 | Thompson | |
| 9,849,010 B2 | 12/2017 | Thompson | |
| 10,130,497 B2 | 11/2018 | Krautkremer et al. | |
| 11,559,412 B2 * | 1/2023 | Gilmartin | A61F 2/848 |
| 2001/0003801 A1 * | 6/2001 | Strecker | A61F 2/954 |
| | | | 623/1.13 |
| 2002/0022875 A1 | 2/2002 | Strecker | |
| 2002/0052649 A1 * | 5/2002 | Greenhalgh | A61F 2/0063 |
| | | | 623/1.36 |
| 2002/0179166 A1 | 12/2002 | Houston et al. | |
| 2003/0040771 A1 | 2/2003 | Hyodoh et al. | |
| 2003/0093145 A1 | 5/2003 | Lawrence-Brown et al. | |
| 2003/0191517 A1 | 10/2003 | Osborne et al. | |
| 2004/0039435 A1 | 2/2004 | Hancock et al. | |
| 2004/0127973 A1 | 7/2004 | Mangiardi et al. | |
| 2004/0193141 A1 | 9/2004 | Leopold et al. | |
| 2005/0033418 A1 | 2/2005 | Banas et al. | |
| 2005/0049682 A1 | 3/2005 | Leanna et al. | |
| 2005/0154448 A1 | 7/2005 | Cully et al. | |
| 2005/0240278 A1 | 10/2005 | Aliski et al. | |
| 2005/0283962 A1 | 12/2005 | Boudjemline | |
| 2006/0265051 A1 | 11/2006 | Caro et al. | |
| 2007/0123969 A1 | 5/2007 | Gianotti | |
| 2007/0282453 A1 | 12/2007 | Weitzner et al. | |
| 2007/0299506 A1 | 12/2007 | Carter et al. | |
| 2008/0228262 A1 | 9/2008 | Goldmann et al. | |
| 2009/0005855 A1 * | 1/2009 | Goto | A61F 2/07 |
| | | | 623/1.15 |
| 2009/0030363 A1 | 1/2009 | Gellman | |
| 2009/0138070 A1 | 5/2009 | Holzer et al. | |
| 2009/0187240 A1 | 7/2009 | Clerc et al. | |
| 2009/0276029 A1 | 11/2009 | Caro et al. | |
| 2010/0030321 A1 | 2/2010 | Mach | |
| 2010/0100170 A1 | 4/2010 | Tan et al. | |
| 2010/0191319 A1 | 7/2010 | Lilburn et al. | |
| 2010/0256731 A1 | 10/2010 | Mangiardi | |
| 2010/0318177 A1 | 12/2010 | Majercak et al. | |
| 2011/0213453 A1 | 9/2011 | Mangiardi | |
| 2011/0307070 A1 | 12/2011 | Clerc et al. | |
| 2012/0116528 A1 | 5/2012 | Nguyen | |
| 2012/0165956 A1 | 6/2012 | Li | |
| 2012/0290100 A1 | 11/2012 | Li | |
| 2012/0296257 A1 | 11/2012 | Van Dam et al. | |
| 2013/0018452 A1 | 1/2013 | Weitzner et al. | |
| 2013/0172983 A1 | 7/2013 | Clerc et al. | |
| 2013/0304098 A1 * | 11/2013 | Mortarino | A61F 2/12 |
| | | | 606/151 |
| 2014/0243992 A1 | 8/2014 | Walsh et al. | |
| 2014/0277560 A1 | 9/2014 | Walak | |
| 2014/0277561 A1 | 9/2014 | Jordan | |
| 2014/0343683 A1 | 11/2014 | Jeon et al. | |
| 2015/0282955 A1 | 10/2015 | Guler et al. | |
| 2016/0058585 A1 | 3/2016 | Seddon et al. | |
| 2016/0100930 A1 | 4/2016 | Walsh et al. | |
| 2017/0119520 A1 * | 5/2017 | Hingston | A61F 2/82 |
| 2019/0029850 A1 | 1/2019 | Keating et al. | |
| 2019/0307586 A1 * | 10/2019 | Gilmartin | A61F 2/86 |
| 2020/0214858 A1 * | 7/2020 | Gilmartin | A61F 2/848 |
| 2022/0096254 A1 * | 3/2022 | Folan | A61F 2/848 |

FOREIGN PATENT DOCUMENTS

| | | |
|---|---|---|
| CN | 102362023 A | 2/2012 |
| DE | 102013221450 A1 | 7/2014 |
| EP | 1258229 A1 | 11/2002 |
| GB | 2512176 A | 9/2014 |
| JP | 2005168757 A | 6/2005 |
| WO | 2008076706 A2 | 6/2008 |
| WO | 201008574 A2 | 7/2010 |
| WO | 2014134352 A1 | 9/2014 |
| WO | 2014164308 A1 | 10/2014 |

OTHER PUBLICATIONS

International Search Report and Written Opinion dated Oct. 9, 2018 for International Application No. PCT/US2018/043863.

International Search Report and Written Opinion dated Aug. 29, 2019 for International Application No. PCT/US2019/026407.

International Search Report and Written Opinion dated Mar. 19, 2020 for International Application No. PCT/US2020/0121373.

* cited by examiner

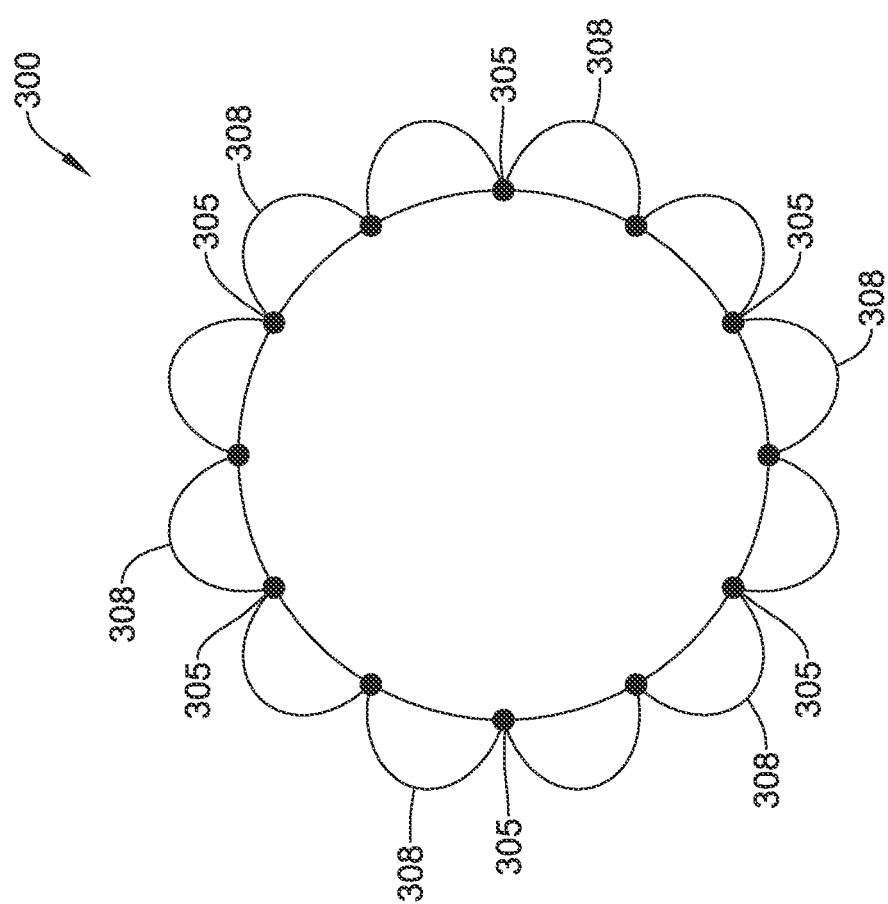

STENT WITH ANTI-MIGRATION FEATURES

CROSS REFERENCE TO RELATED APPLICATIONS

This application claims the benefit of and priority to U.S. Provisional Patent Application Ser. No. 63/084,865 filed on Sep. 29, 2020, the disclosure of which is incorporated herein by reference.

TECHNICAL FIELD

The present disclosure pertains to medical devices, methods for manufacturing medical devices, and uses thereof. More particularly, the present disclosure pertains to a stent for implantation in a body lumen, and associated methods.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods.

SUMMARY

This disclosure provides design, material, manufacturing method, and use alternatives for medical devices. An example medical device may include a stent.

In a first example, a stent may comprise an elongated tubular member comprising at least one knitted filament having a plurality of twisted knit stitches with intermediate rung portions extending between adjacent twisted knit stitches. The elongated tubular member may be configured to move between a collapsed configuration and an expanded configuration. The elongated tubular member may further comprise one or more anti-migration features formed in one or more of the intermediate rung portions. When the elongated tubular member is in the expanded configuration, the one or more anti-migration features may extend radially therefrom.

Alternatively or additionally to any of the examples above, in another example, the one or more anti-migration features may extend in the range of 1 to 4 millimeters radially beyond a base diameter of the elongated tubular member in the expanded configuration.

Alternatively or additionally to any of the examples above, in another example, when the elongated tubular member is in the expanded configuration the one or more anti-migration features may extend at a non-parallel angle relative to a longitudinal axis of the elongated tubular body.

Alternatively or additionally to any of the examples above, in another example, when the elongated tubular member is in the expanded configuration the one or more anti-migration features may include a distally oriented apex.

Alternatively or additionally to any of the examples above, in another example, when the elongated tubular member is in the expanded configuration the one or more anti-migration features may bend back on itself.

Alternatively or additionally to any of the examples above, in another example, the one or more anti-migration features may each include a first joint bend adjacent a first twisted knit stitch and a second joint bend adjacent a second twisted knit stitch.

Alternatively or additionally to any of the examples above, in another example, the first and second joint bends may be configured to cause the anti-migration loop to lie flat as the elongated tubular body is moved from the expanded configuration to the collapsed configuration.

Alternatively or additionally to any of the examples above, in another example, when the elongated tubular member is in the collapsed configuration at least a portion of the one or more anti-migration features may be subsumed into one or more adjacent twisted knit stitches.

Alternatively or additionally to any of the examples above, in another example, a length of the intermediate rung portions in the collapsed configuration may be less than a length of the intermediate rung portions in the expanded configuration.

Alternatively or additionally to any of the examples above, in another example, at least some of the plurality of twisted knit stitches are suspended from a twisted knit stitch in a preceding row.

Alternatively or additionally to any of the examples above, in another example, a diameter of the elongated tubular member in the collapsed configuration may be in the range of about 60% to 80% less than a diameter of the elongated tubular member in the expanded configuration.

In another example, a method of manufacturing a stent having anti-migration features may comprise knitting a stent blank, the knitted stent blank may include at least one knitted filament having a plurality of twisted knit stitches with intermediate rung portions extending between adjacent twisted knit stitches, disposing a knitted stent blank in position over a mandrel, the mandrel including one or more anti-migration feature forming elements, engaging one or more intermediate rung portions of the knitted stent with the one or more anti-migration feature forming elements to form an anti-migration feature having a first point bend and a second point bend, annealing the woven stent blank while disposed on the mandrel to form a shaped stent with the anti-migration feature, and disengaging the one or more anti-migration feature forming elements in order to remove the shaped stent from the mandrel.

Alternatively or additionally to any of the examples above, in another example, the one or more anti-migration feature forming elements may comprise pins that are configured to be driven in a radially outward direction relative to a central longitudinal axis of the mandrel, and engaging the wire with the one or more anti-migration feature forming elements may comprise driving the pins in the radially outward direction relative to the central longitudinal axis of the mandrel.

Alternatively or additionally to any of the examples above, in another example, disengaging the one or more anti-migration feature forming elements may comprise permitting the pins to move in a radially inward direction relative to the central longitudinal axis of the mandrel.

Alternatively or additionally to any of the examples above, in another example, disposing the knitted stent blank in position over the mandrel may comprise stretching the knitted stent blank over the mandrel and allowing the knitted stent blank to conform to an outer surface of the mandrel.

In another example, a stent may comprise an elongated tubular member comprising at least one knitted filament having a plurality of twisted knit stitches with intermediate rung portions extending between adjacent twisted knit stitches, the elongated tubular member may be configured to move between a collapsed configuration and an expanded configuration and one or more anti-migration features formed in one or more of the intermediate rung portions. When the elongated tubular member is in the expanded configuration, the one or more anti-migration features may extend radially therefrom.

Alternatively or additionally to any of the examples above, in another example, the one or more anti-migration features may extend in the range of 1 to 4 millimeters radially beyond a base diameter of the elongated tubular member in the expanded configuration.

Alternatively or additionally to any of the examples above, in another example, when the elongated tubular member is in the expanded configuration the one or more anti-migration features may extend at a non-parallel angle relative to a longitudinal axis of the elongated tubular body.

Alternatively or additionally to any of the examples above, in another example, when the elongated tubular member is in the expanded configuration the one or more anti-migration features may include a distally oriented apex.

Alternatively or additionally to any of the examples above, in another example, when the elongated tubular member is in the expanded configuration the one or more anti-migration features may bend back on itself.

Alternatively or additionally to any of the examples above, in another example, the one or more anti-migration features may each includes a first joint bend adjacent a first twisted knit stitch and a second joint bend adjacent a second twisted knit stitch.

Alternatively or additionally to any of the examples above, in another example, the first and second joint bends may be configured to cause the anti-migration loop to lie flat as the elongated tubular body is moved from the expanded configuration to the collapsed configuration.

Alternatively or additionally to any of the examples above, in another example, when the elongated tubular member is in the collapsed configuration at least a portion of the one or more anti-migration features may be subsumed into one or more adjacent twisted knit stitches.

Alternatively or additionally to any of the examples above, in another example, a length of the intermediate rung portions in the collapsed configuration may be less than a length of the intermediate rung portions in the expanded configuration.

Alternatively or additionally to any of the examples above, in another example, a diameter of the elongated tubular member in the collapsed configuration may be in the range of about 60% to 80% less than a diameter of the elongated tubular member in the expanded configuration.

In another example, a stent may comprise an elongated tubular member comprising at least one knitted filament having a plurality of twisted knit stitches each including a loop portion and an overlapping base region with intermediate rung portions extending between adjacent twisted knit stitches and at least some of the plurality of twisted knit stitches are suspended from an intermediate rung portion of a preceding row, the elongated tubular member configured to move between a collapsed configuration and an expanded configuration and one or more anti-migration features formed in one or more of the intermediate rung portions. When the elongated tubular member is in the expanded configuration, the one or more anti-migration features may extend radially therefrom.

Alternatively or additionally to any of the examples above, in another example, the one or more anti-migration features may be positioned at a similar longitudinal location about a circumference of the elongated tubular member.

Alternatively or additionally to any of the examples above, in another example, the one or more anti-migration features may extend in the range of 1 to 4 millimeters radially beyond a base diameter of the elongated tubular member in the expanded configuration.

Alternatively or additionally to any of the examples above, in another example, when the elongated tubular member is in the expanded configuration the one or more anti-migration features may extend at a non-parallel angle relative to a longitudinal axis of the elongated tubular body.

Alternatively or additionally to any of the examples above, in another example, when the elongated tubular member is in the expanded configuration the one or more anti-migration features may bend back on itself.

Alternatively or additionally to any of the examples above, in another example, the one or more anti-migration features may each include a first joint bend adjacent an overlapping base region of a first twisted knit stitch and a second joint bend adjacent an overlapping base region of a second twisted knit stitch.

In another example, a method of manufacturing a stent having anti-migration features may comprise knitting a stent blank, the knitted stent blank including at least one knitted filament having a plurality of twisted knit stitches with intermediate rung portions extending between adjacent twisted knit stitches, disposing a knitted stent blank in position over a mandrel, the mandrel including one or more anti-migration feature forming elements, engaging one or more intermediate rung portions of the knitted stent with the one or more anti-migration feature forming elements to form an anti-migration feature having a first point bend and a second point bend, annealing the woven stent blank while disposed on the mandrel to form a shaped stent with the anti-migration feature, and disengaging the one or more anti-migration feature forming elements in order to remove the shaped stent from the mandrel.

Alternatively or additionally to any of the examples above, in another example, the one or more anti-migration feature forming elements may comprise pins that are configured to be driven in a radially outward direction relative to a central longitudinal axis of the mandrel, and engaging the wire with the one or more anti-migration feature forming elements comprises driving the pins in the radially outward direction relative to the central longitudinal axis of the mandrel.

Alternatively or additionally to any of the examples above, in another example, disengaging the one or more anti-migration feature forming elements may comprise permitting the pins to move in a radially inward direction relative to the central longitudinal axis of the mandrel.

Alternatively or additionally to any of the examples above, in another example, disposing the knitted stent blank in position over the mandrel may comprise stretching the knitted stent blank over the mandrel and allowing the knitted stent blank to conform to an outer surface of the mandrel.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments in connection with the accompanying drawings, in which:

FIGS. 12A-12D are schematic illustrations of anti-migration features that a knitted stent may include;

Figure 1:
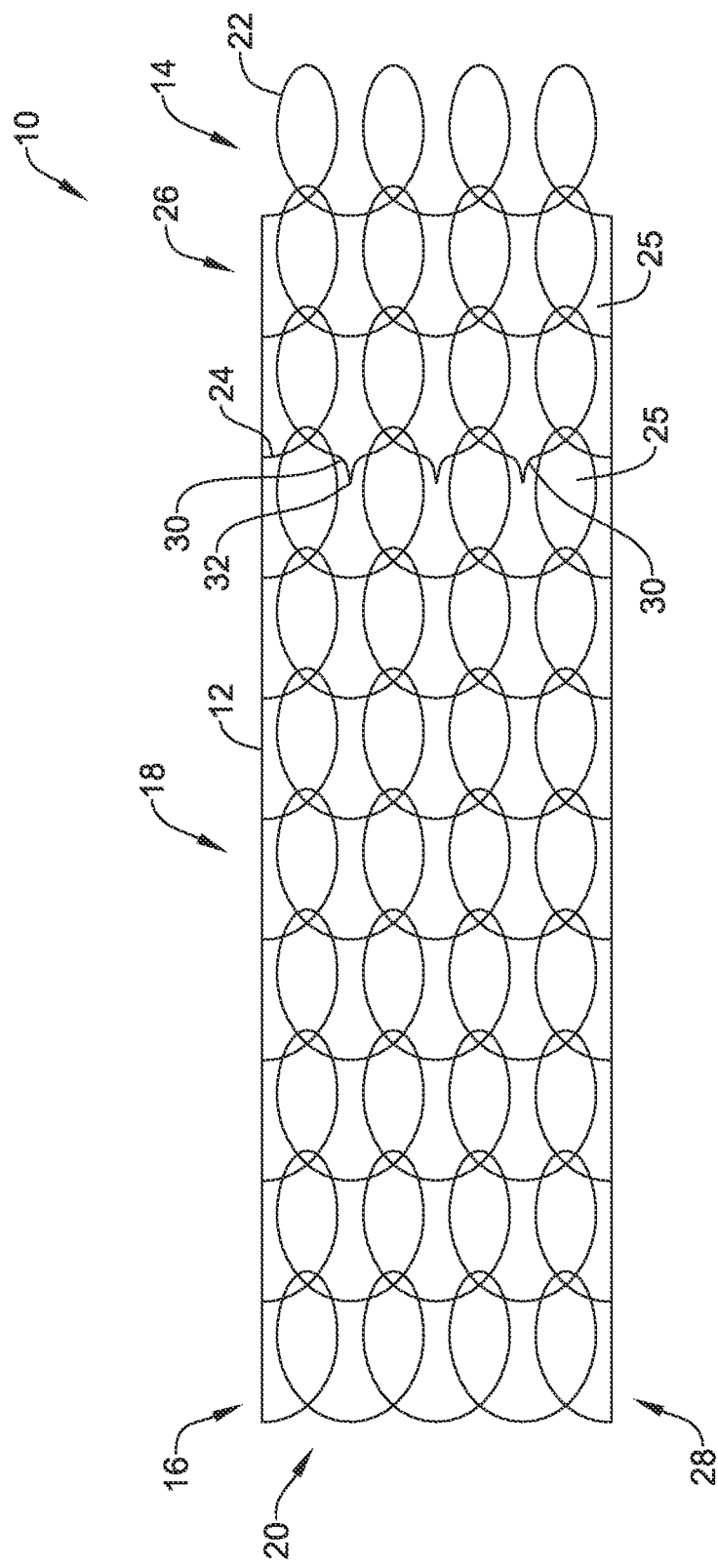
FIG. 1 is a side view of an illustrative stent.

While the disclosure is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

In some instances, it may be desirable to provide an endoluminal implant, or stent, that can deliver luminal patency in a patient with an esophageal stricture or other medical condition. Such stents may be used in patients experiencing dysphagia, sometimes due to esophageal cancer. An esophageal stent may allow a patient to maintain nutrition via oral intake during cancer treatment or palliation periods. Current gastrointestinal (GI) stenting regimes for the treatment of vessel strictures may rely on a self-expanding stent (SES) to to resolve underlying stricture while remaining in-situ. However, this type of stenting may have a high prevalence for migration, particularly in fully covered designs. Some stents may include protrusions (e.g., loops, quills, etc.) that radially protrude out from the stent body. These raised features may interact with the duct of vessel to reduce device migration. However, these devices may be difficult to remove or reposition as they may be difficult to purse down to lower diameters. Further, devices with these types of protrusions (or anti-migration features) may be indicated for permanent implantation. Where these devices are desired to be removable, retraction or repositioning of the devices may be limited as the angulation of the protrusions may cause vessel damage with movement of the stent. What may be desirable is an endoluminal implant or stent that includes anti-migration features and can also be readily pursed down for repositioning and/or removal. While the embodiments disclosed herein are discussed with reference to esophageal stents, it is contemplated that the stents described herein may be used and sized for use in other locations such as, but not limited to: bodily tissue, bodily organs, vascular lumens, non-vascular lumens and combinations thereof, such as, but not limited to, in the coronary or peripheral vasculature, trachea, bronchi, colon, small intestine, biliary tract, urinary tract, prostate, brain, stomach and the like.

FIG. 1 illustrates a side view of an illustrative endoluminal implant 10, such as, but not limited to, a stent. In some instances, the stent 10 may be formed from an elongated tubular member 12. While the stent 10 is described as generally tubular, it is contemplated that the stent 10 may take any cross-sectional shape desired. The stent 10 may have a first, or proximal end 14, a second, or distal end 16, and an intermediate region 18 disposed between the first end 14 and the second end 16. The stent 10 may include a lumen 20 extending from a first opening adjacent the first end 14 to a second opening adjacent to the second end 16 to allow for the passage of food, fluids, etc.

The stent 10 may be expandable from a first radially collapsed configuration (not explicitly shown) to a second radially expanded configuration. In some cases, the stent 10 may be deployed to a configuration between the collapsed configuration and a fully expanded configuration. The stent 10 may be structured to extend across a stricture and to apply a radially outward pressure to the stricture in a lumen to open the lumen and allow for the passage of foods, fluids, air, etc. When the stent 10 is in a radially collapsed configuration, the outer diameter of the stent 10 is reduced relative to a fully or partially expanded configuration. In some cases, to reduce the diameter of the stent 10 for delivery to the target location, the stent 10 is stretched or lengthened. When the stent 10 is deployed (moved from the delivery configuration to an expanded configuration), the length of the stent 10 decreases and the diameter increases. In some cases, stents 10 may experience in the range of about 20% to about 40% foreshortening (e.g., the percentage by which the length of a stent decreases from its delivery configuration to its expanded configuration). It is contemplated that the change in length and/or the change in diameter of the stent 10 may be at least partially dependent on a size (e.g., diameter) of the stent. In some cases, a biliary stent may have a deployed diameter in the range of about 8 millimeters to about 10 millimeters and a constrained diameter of about 2.5 millimeters to about 3 millimeters. This may correspond to about a 60% to about 80% reduction in diameter from the expanded configuration to the delivery configuration. This is just an example. The reduction in diameter may be less than 60% or greater than 80%, as desired. In another example, an endoscopy stent may have a deployed diameter in the range of about 18 millimeters to about 23 millimeters and a constrained diameter of about 6 millimeters to about 6.5 millimeters. This may correspond to about a 60% to about 80% reduction in diameter from the expanded configuration to the delivery configuration. This is just an example. The reduction in diameter may be less than 60% or greater than 80%, as desired.

The proximal end 14 of the stent 10 may include a plurality of loops 22. The loops 22 may be configured to receive a retrieval tether or suture interwoven therethrough, or otherwise passing through one or more of the loops 22. The retrieval suture may be used to collapse and retrieve the stent 10, if so desired. For example, the retrieval suture may be pulled like a drawstring to radially collapse the proximal end 14 of the stent 10 to facilitate removal of the stent 10 from a body lumen.

The stent 10 may have a knitted structure, fabricated from a single filament 24 interwoven with itself and defining open cells 25. In some cases, the filament 24 may be a monofilament, while in other cases the filament 24 may be two or more filaments wound, braided, or woven together. In some instances, an inner and/or outer surface of the stent 10 may be entirely, substantially, or partially, covered with a polymeric covering or coating. The covering or coating may extend across and/or occlude one or more, or a plurality of the cells 25 defined by the struts or filaments 24. The covering or coating may help reduce food impaction and/or tumor or tissue ingrowth.

It is contemplated that the stent 10 can be made from a number of different materials such as, but not limited to, metals, metal alloys, shape memory alloys and/or polymers, as desired, enabling the stent 10 to be expanded into shape when accurately positioned within the body. In some instances, the material may be selected to enable the stent 10 to be removed with relative ease as well. For example, the stent 10 can be formed from alloys such as, but not limited to, Nitinol and Elgiloy®. Depending on the material selected for construction, the stent 10 may be self-expanding (i.e., configured to automatically radially expand when unconstrained). In some embodiments, fibers may be used to make the stent 10, which may be composite fibers, for example, having an outer shell made of Nitinol having a platinum core. It is further contemplated the stent 10 may be formed from polymers including, but not limited to, polyethylene terephthalate (PET). In some embodiments, the stent 10 may be self-expanding while in other embodiments, the stent 10 may be expanded by an expansion device (such as, but not limited to a balloon inserted within the lumen 20 of the stent 10). As used herein the term "self-expanding" refers to the tendency of the stent to return to a preprogrammed diameter when unrestrained from an external biasing force (for example, but not limited to, a delivery catheter or sheath). The stent 10 may include a one-way valve, such as an elastomeric slit valve or duck bill valve, positioned within the lumen 20 thereof to prevent retrograde flow of gastrointestinal fluids.

In some instances, in the radially expanded configuration, the stent 10 may include a first end region 26 proximate the proximal end 14 and a second end region 28 proximate the second end 16. In some embodiments, the first end region 26 and the second end region 28 may include retention features or anti-migration flared regions (not explicitly shown) having enlarged diameters relative to the intermediate portion 18. The anti-migration flared regions, which may be positioned adjacent to the first end 14 and the second end 16 of the stent 10, may be configured to engage an interior portion of the walls of the esophagus or other body lumen. In some embodiments, the retention features, or flared regions may have a larger diameter than the cylindrical intermediate region 18 of the stent 10 to prevent the stent 10 from migrating once placed in the esophagus or other body lumen. It is contemplated that a transition from the cross-sectional area of the intermediate region 18 to the retention features or flared regions may be gradual, sloped, or occur in an abrupt step-wise manner, as desired.

In some embodiments, the first anti-migration flared region may have a first outer diameter and the second anti-migration flared region may have a second outer diameter. In some instances, the first and second outer diameters may be approximately the same, while in other instances, the first and second outer diameters may be different. In some embodiments, the stent 10 may include only one or none of the anti-migration flared regions. For example, the first end region 26 may include an anti-migration flare while the second end region 28 may have an outer diameter similar to the intermediate region 18. It is further contemplated that the second end region 28 may include an anti-migration flare while the first end region 26 may have an outer diameter similar to an outer diameter of the intermediate region 18. In some embodiments, the stent 10 may have a uniform outer diameter from the first end 14 to the second end 16. In some embodiments, the outer diameter of the intermediate region 18 may be in the range of 15 to 25 millimeters. The outer diameter of the anti-migration flares may be in the range of 20 to 30 millimeters. It is contemplated that the outer diameter of the stent 10 may be varied to suit the desired application.

The stent 10 may further include one or more radially extending anti-migration features 30. As will be described in more detail herein, the anti-migration features 30 may be portions or loops of the filament 24 which extend radially from the stent body 12. For example, the anti-migration features 30 may have an outer diameter that is greater than the intermediate region 18 and/or greater than an anti-migration flared region (if so provided). In some cases, the anti-migration features 30 may extend in the range of about 1 millimeter to about 4 millimeters beyond the base diameter of the stent 10. The base diameter may be the nominal (e.g., substantially constant) outer diameter of the body 12 of the stent 10 taken at a same longitudinal location as the anti-migration features 30. When the stent 10 is in the expanded configuration, the anti-migration features 30 may extend at a non-parallel angle relative to a longitudinal axis of the stent 10. It is contemplated that an angle of the anti-migration features 30 may be determined, at least in part, on a length of the anti-migration features 30. For example, to reduce the risk of puncture, longer anti-migration features 30 may be oriented at smaller angles relative to the longitudinal axis of the stent 10 than shorter anti-migration features. This is just an example. In some cases, when the stent 10 is covered or partially covered with a covering or coating, the anti-migration features 30 may be left bare or uncovered (e.g., free from a covering or coating) to allow for tissue ingrowth to further reduce migration of the stent 10. However, this is not required. In some cases, the anti-migration features 30 may include the covering or coating.

In some cases, the anti-migration features 30 may be circumferentially arranged about a perimeter of the stent 10 at a similar longitudinal position. However, it is contemplated that the anti-migration features 30 may be arranged at one or more different locations along the length of the stent 10, if desired. It is further contemplated the anti-migration features 30 may be provided in circumferential rows or as discrete features (e.g., not necessarily extending about a circumference of the stent 10), as desired. When provided as discrete features, the anti-migration features 30 may be asymmetrically or randomly positioned or arranged in a pattern that does not necessarily include complete circumferential rows. For example, patterns may include, but are not limited to staggered or alternating anti-migration features 30.

In some cases, the anti-migration features 30 may be formed such that an apex 32 of the anti-migration features 30 is angled in a generally distal direction. Such an orientation may help limit distal movement of the stent 10 when implanted. However, other configurations may be used as desired. In some cases, the anti-migration features 30 may be formed such that the apex 32 is angled in a proximal direction. In yet other cases, the stent 10 may include a combination of distally angled and proximally angled anti-migration features 30. It is contemplated that the apex 32 of the anti-migration features 30 may be curved or bent back over a length of the anti-migration features 30 such that the apex 32 is not in contact with the tissue (e.g., to form a more atraumatic anti-migration feature), as will be described in more detail herein.

It is contemplated that the stent 10 can be made from a number of different materials such as, but not limited to, metals, metal alloys, shape memory alloys and/or polymers, as desired, enabling the stent 10 to be expanded into shape when accurately positioned within the body. In some instances, the material may be selected to enable the stent 10 to be removed with relative ease as well. For example, the stent 10 can be formed from alloys such as, but not limited to, Nitinol and Elgiloy®. Depending on the material selected for construction, the stent 10 may be self-expanding or require an external force to expand the stent 10. In some embodiments, composite filaments may be used to make the stent 10, which may include, for example, an outer shell or cladding made of Nitinol and a core formed of platinum or other radiopaque material. It is further contemplated the stent 10 may be formed from polymers including, but not limited to, polyethylene terephthalate (PET). In some instances, the filaments of the stent 10, or portions thereof, may be bioabsorbable or biodegradable, while in other instances the filaments of the stent 10, or portions thereof, may be biostable.

Figure 2:
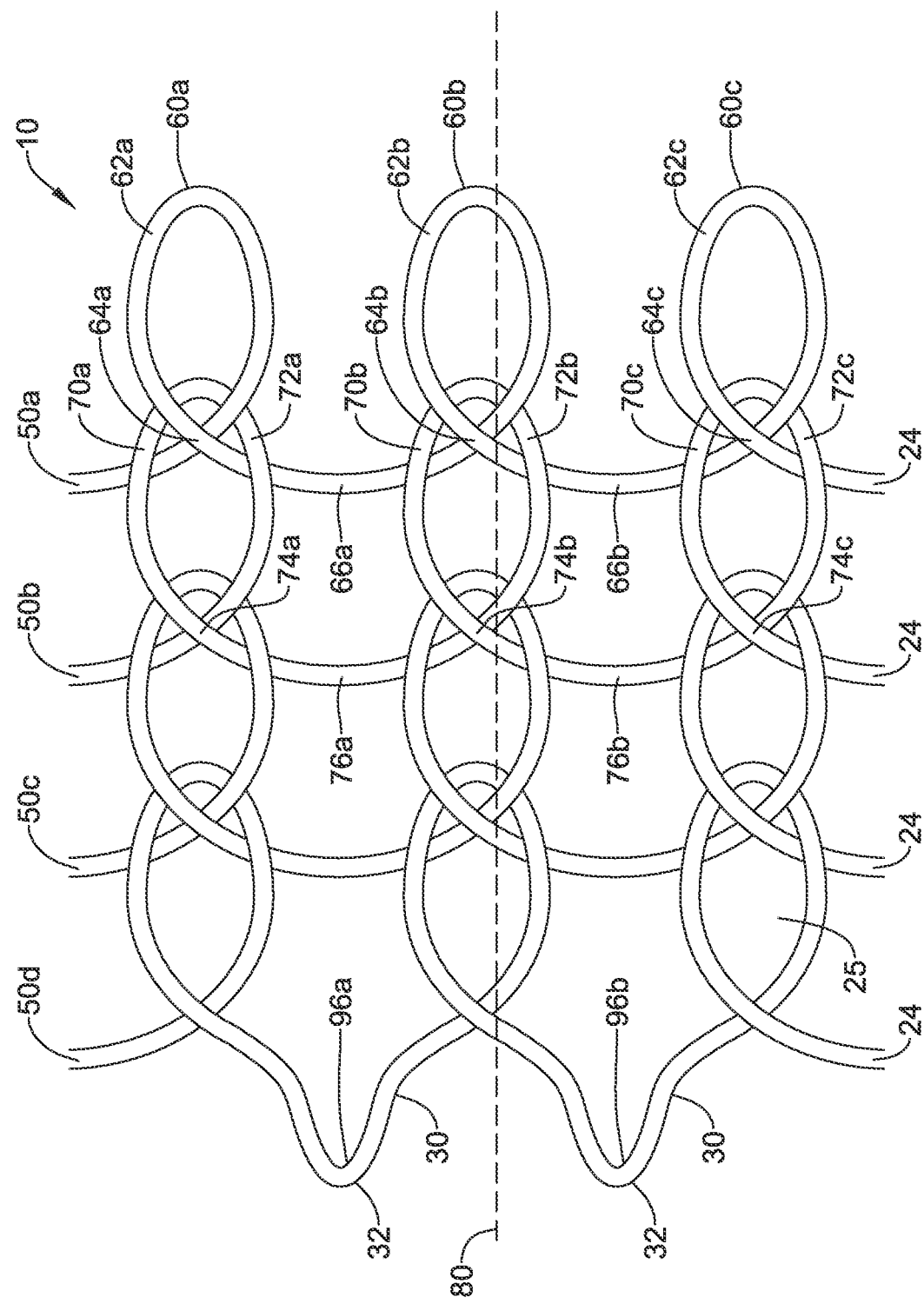
FIG. 2 is an enlarged side view of a portion of the illustrative stent of FIG. 1.

FIG. 2 illustrates a partial enlarged side view of the knitted configuration of the stent 10. The stent 10 may include a plurality of rows 50a, 50b, 50c, 50d (collectively, 50) extending circumferentially about the stent 10. The stent 10 may include any number of rows 50 desired. For example, the number of rows 50 may be selected to achieve a desired length of the stent 10. The uppermost, or first, row 50a may be unsecured and active. In some instances, the first row 50a may include a plurality of loops 60a, 60b, 60c (collectively, 60). The loops 60 may each include a loop portion 62a, 62b, 62c (collectively, 62) and an overlapping base portion 64a, 64b, 64c (collectively, 64). The overlapping base portion 64a, 64b, 64c is understood as the portion of the loops 60 in which one segment of the filament overlaps or crosses over a second segment of the filament, with the segment of the filament forming the loop portion 62a, 62b, 62c extending therebetween. Adjacent loops 60 may be interconnected by a rung section 66a, 66b (collectively, 66). For example, a first rung section 66a may extend between the base portion 64a of the first loop 60a and the base portion 64b of the second loop 60b. The next row 50b may be suspended from the loops 60 of the first row 50a. For example, the second row 50b may include a plurality of loops 70a, 70b, 70c (collectively, 70) each including a loop portion 72a, 72b, 72c (collectively, 72) and a base portion 74a, 74b, 74c (collectively, 74). Adjacent loops 70 may be interconnected by a rung section 76a, 76b (collectively, 76). As the stent 10 is knitted, the loop portion 72 may be wrapped about the base portion 64 of the preceding row 50a.

It is contemplated that a single row 50 may be formed at a time. For example, the rows may be formed in succession with a subsequent row (e.g., row 50b) being formed after the preceding row (e.g., row 50a) has formed a complete rotation. While not explicitly shown, the loops 60 of the first row 50a may be wrapped about a section of the filament 24 free from loops. As described herein, the loops 70 of the second row 50b may be wrapped about the base portion 64 of the loops 60 the preceding row 50a. For example, the filament 24 may be knitted such that it extends from the first rung section 76a, is wrapped about the base portion 64b of the preceding row 50a, crosses back over itself to form base section 74b and continues to the next rung section 76b. It is contemplated that the loop portion 70 may be positioned on a first side of the rungs 66a, 66b and on a second opposite side of the loop portion 62b. In other words, the filament 24 may be wound such that it extends on top of the second rung portion 66b, behind the base portion 64b, and over the first rung portion 66a before crossing over itself to form the base portion 74b of the loop 70b of the second row 50b. The reverse configuration is also contemplated in which the filament 24 may be wound such that it extends behind the second rung portion 66b, over or on top of the base portion 64b, and behind the first rung portion 66a before crossing over itself to form the base portion 74b of the loop 70b of the second row 50b.

Figure 3:
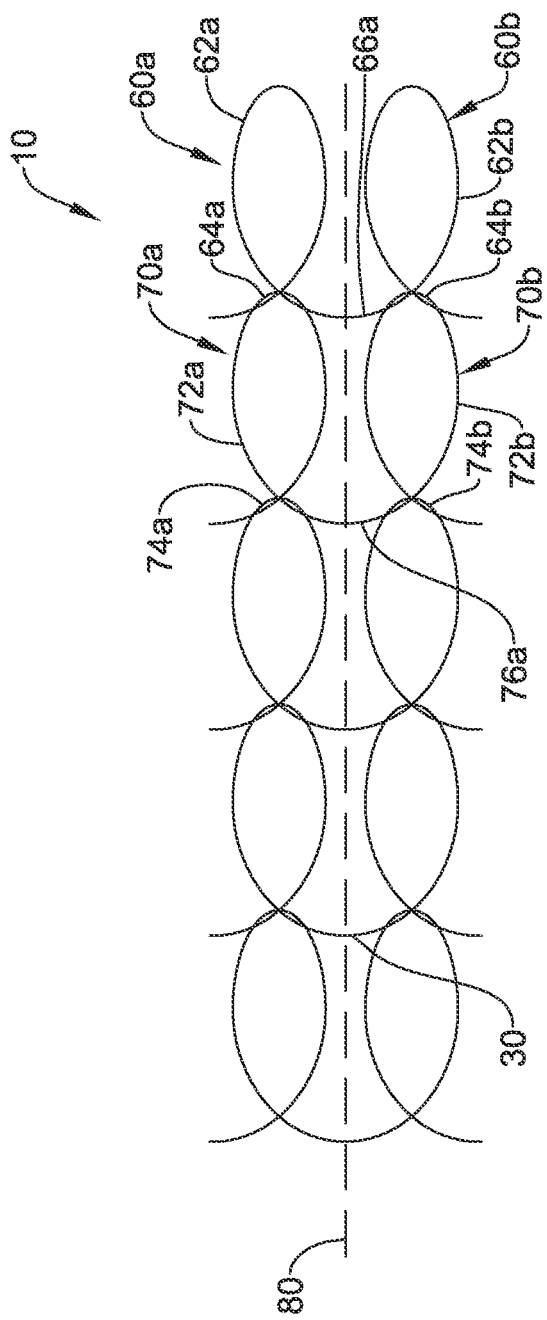
FIG. 3 is a partial side view of the illustrative stent of FIG. 1 in an elongated configuration.

The knitted structure of the stent 10 may allow the loop sections 62, 72 to lengthen or contract such that the cells 25 and/or loop sections 62, 72 have a first profile when the stent 10 is in the expanded configuration and a second profile, different from the first profile, when the stent 10 is in a collapsed delivery configuration. Lengthening of the loop sections 62, 72 may allow the cross-sectional diameter of the stent 10 to be reduced for delivery. To lengthen, the loops 60, 70 use some of the length of the filament 24 from the rungs 66, 76 to elongate. FIG. 3 illustrates a portion of the stent 10 in an elongated configuration. As can be seen, as the loops 60, 70 elongate, the rung material 66, 76 is pulled into the loop portion 62, 72 to allow for loop elongation (e.g., in a direction along a longitudinal axis 80) while the intermediate rung portion 66, 76 is shortened. The rung material 66, 76 may be accessible and readily subsumed into the loop portion 62, 72 due to the twist region 64, 74. Similarly, the anti-migration features 30 are readily subsumed into the loop portions. This may result in the stent 10 being constrained at lower forces allowing it to be loaded into a coaxial delivery system. It is contemplated that the knit structure of the stent 10 may be less subject to wire breaks due to fatigue from peristaltic motion, when compared to previous knit for stents. The softer curvature of the current knit pattern may allow the loops 60, 70 be easily pursed by external forces which may be applied to the stent 10 by the anatomy. It is contemplated that stent 10 may be heat treated or annealed in the expanded configuration such that when the external force is released, the anti-migration features 30 may readily resume the radially outwardly extending configuration while the diameter of the stent 10 expands.

Once the stent 10 has been deployed, the stent 10 can be elongated (thus reducing the diameter) to remove or reposition the stent 10. To collapse the stent 10 for repositioning or removal, the stent 10 may be actuated from either or both of the proximal end 14 or the distal end 16 of the stent 10. In some cases, a pull wire may be used to facilitate collapse of the stent 10. However, other actuation mechanisms may be used as desired. For example, a physician may use one or more forceps to grip one or both ends of the stent 10. It is contemplated that in the range of about 60% to about 80% of the length of the stent 10 may experience a diameter reduction before the stent 10 easily moves within the body lumen. As the diameter of the stent 10 may reduce first at the end experiencing the actuation force, the clinician can select an end of the stent 10 to actuate based on a desired movement of the stent 10.

Returning to FIG. 2, the anti-migration features 30 may be formed in the interconnecting rung sections 96a, 96b (collectively, 96) of one of the rows 50d. While FIG. 2 illustrates the anti-migration features 30 in a single row 50d, it is contemplated that any number of the rows 50 at any longitudinal location may include anti-migration features 30. It is further contemplated that not every rung 96 may be formed into an anti-migration feature 30. For example, in some cases, every other rung 96 may be formed into an anti-migration feature. Other patterned configurations, asymmetric configurations, and/or random configurations for the anti-migration features 30 may be used as desired. The anti-migration features 30 may extend radially outward from the body 12 of the stent 10 and at a generally non-parallel angle relative to the longitudinal axis 80. In some cases, the apexes 32 of the anti-migration features 30 may be pointed in a generally distal direction. In other cases, the apexes 32 of the anti-migration features 30 may be pointed in a generally proximal direction (see, for example, FIG. 11B). In yet other cases, the stent 10 may include one or more anti-migration features 30 pointing distally and one or more anti-migration features 30 pointing proximally. It is further contemplated that one or more of the apexes 32 may be curled back on itself such that the apex 32 is generally pointed in a direction different from the general direction of the anti-migration features 30 (see, for example, FIG. 11C). In some cases, the stent 10 may be formed by first forming a constant diameter stent blank, then stretching the constant diameter stent blank over a mandrel prior to a shaping process and/or an annealing process. However, this is not required. In some cases, the stent 10 may be formed by knitting the stent 10 directly over a shaped mandrel. The formation of the anti-migration features 30 will be described in more detail herein.

Figure 4:
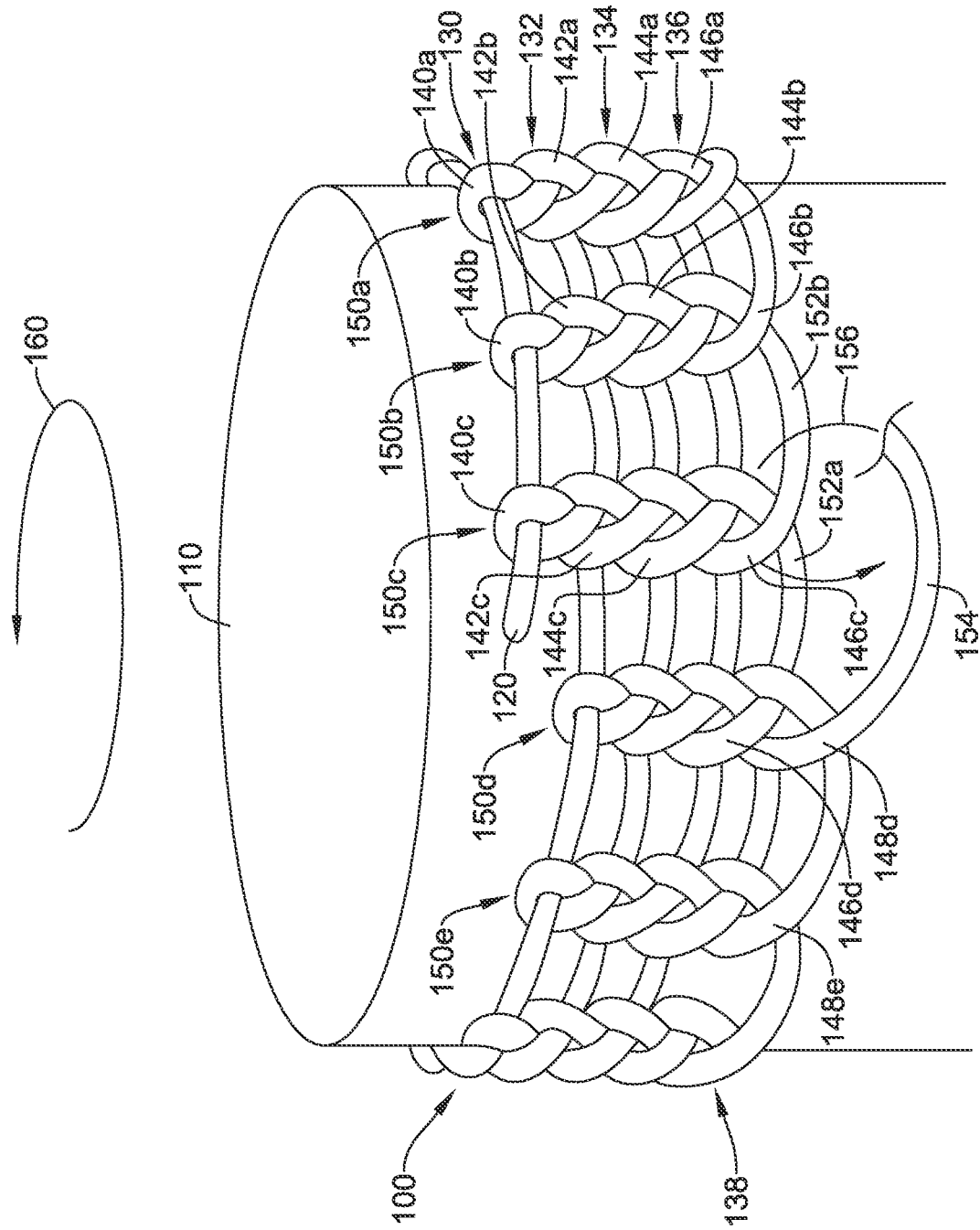
FIG. 4 is an illustrative method of forming a stent.

FIG. 4 illustrates a side view of an illustrative stent 100 being formed about a constant diameter mandrel 110. The stent 100 may be similar in form and function to the stent 10 described above. The stent 100 may be formed from a single knitted strand or filament 120. In general, the stent 100 is formed by knitting in a single direction. For example, in the embodiments illustrated in FIG. 4, the strand 120 is knitted in a counterclockwise direction as shown at arrow 160. However, it should be understood that the stent 100 may be formed by knitting in a clockwise direction, as desired. The strand 120 may follow a looped path about the mandrel 110 configured to form a plurality of interconnected loops.

The strand 120 may be manipulated (e.g., knitted) into a plurality of rows 130, 132, 134, 136, 138 each having a plurality of interconnected or intermeshing loops 140a-c, 142a-c, 144a-c, 146a-c, 148d-e. The stent 100 may include as many rows as required to form a stent 100 having the desired length. As described above, the loops may be loosely knit and include interconnecting intermediate rung portions such as the rung portions 152a and 152b interconnecting three loops 146d, 146c, 146b of one of the rows 136. It should be understood that as the stent 100 is formed from a single strand 120, the rows 130, 132, 134, 136, 138 may not be distinct and separate rows but instead form a continuous connection with the preceding and/or following row. It is further contemplated that the stent 100 need not be formed from a single strand 120 but rather may include two or more strands knitted together. In some instances, a loop may be generally aligned with, or suspended from, a loop of the preceding row in a direction generally parallel to a longitudinal axis of the stent 100 (for example, circumferentially aligned along a length of the stent 100). As can be seen, the loop 146b in one row 136 is suspended from the loop 144b in the row 134 above it. Thus, the loops may form axially extending columns or wales 150a-e, although this is not required.

To form the stent 100, an end region 154 of the strand 120 is passed over an intermediate rung portion 152b of a preceding row 136, as shown at arrow 156. The end region 154 of the strand 120 may then be wrapped behind the loop 146c in a direction opposite to the general direction 160 of the overall knit. The end region 154 of the strand 120 may then be passed over a rung portion 152a on opposing side of the loop 146c (relative to the rung portion 152b) before being crossed over itself to complete the loop. The reverse configuration is also contemplated in which the loop passes behind the rung portions 152b, 152a and over the loop 146c. The loops 140a-c, 142a-c, 144a-c, 146a-c, 148d-e may generally take the form of a twisted knit stitch where each individual loop is twisted. It is contemplated that the twisted nature of the loops may create ridges in the outer surface of the stent 100. These ridges may help secure the stent 100 within the body lumen.

Figure 5:
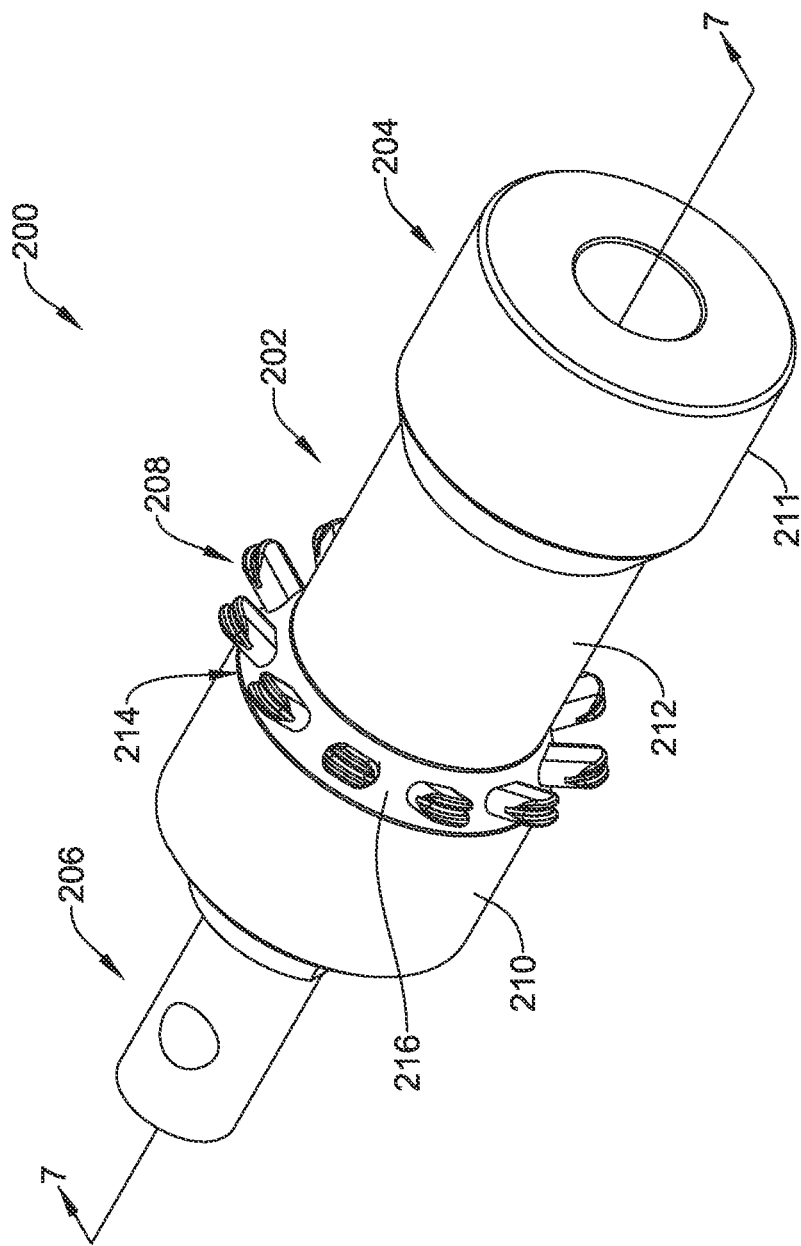
FIG. 5 is a perspective view of an adjustable mandrel.

FIG. 5 is a perspective view of a mandrel 200 for forming a stent having anti-migration features, such as the stent 10 described herein. Some illustrative mandrels are described in commonly assigned U.S. Patent Publication Number 2019/0029850, entitled ADJUSTABLE MANDREL FOR FORMING STENT WITH ANTI-MIGRATION FEATURES, the disclosure of which is hereby incorporated by reference. As described above, in some instances, the stent may additionally include a tapered outer profile region with one or more flared end regions as well as anti-migration features. In some cases, the stent may be considered as having an hourglass profile, for example. However, in other instances, the stent may have a generally constant outer diameter with one or more anti-migration features extending radially outward therefrom.

Figure 6:
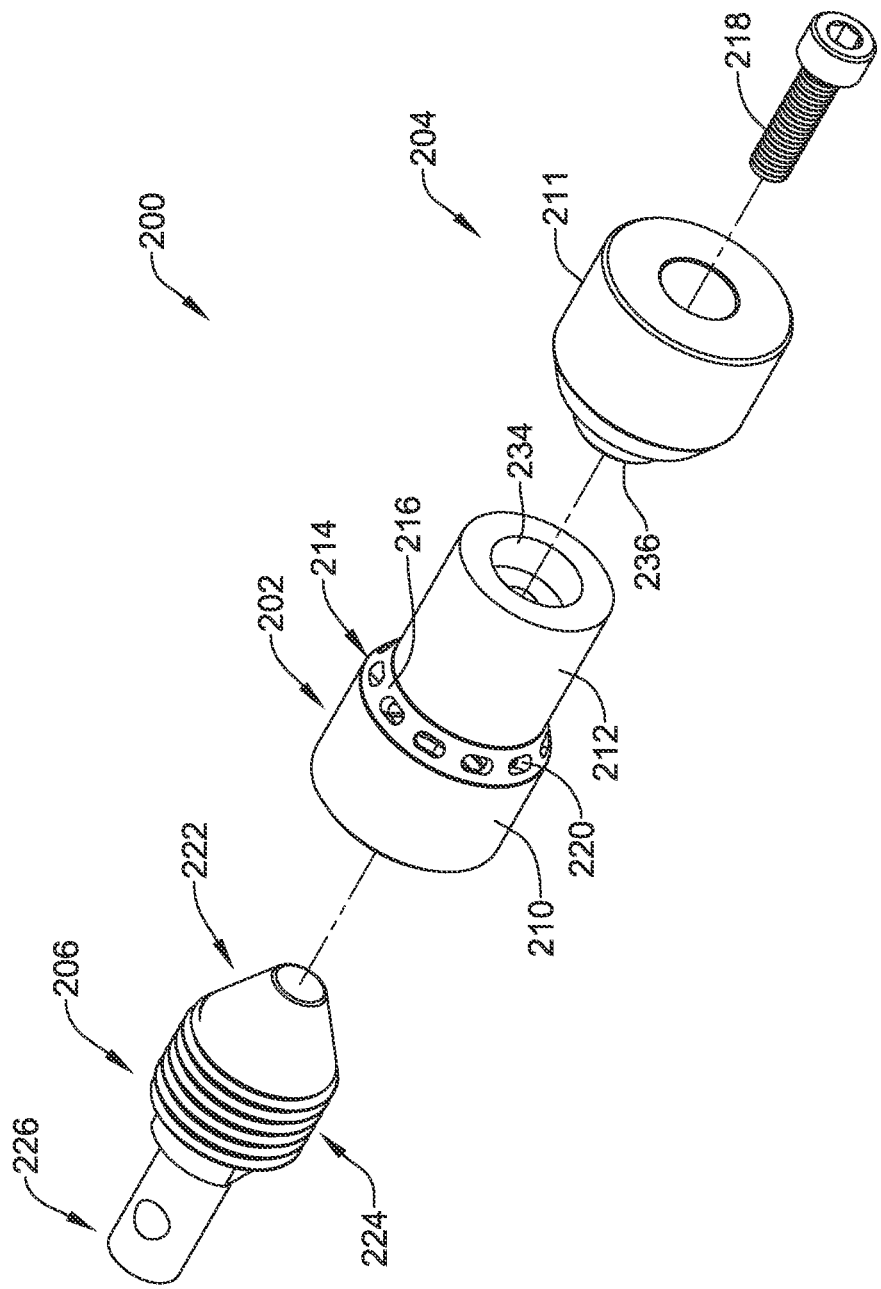
FIG. 6 is an exploded perspective view of the adjustable mandrel of FIG. 5.

As can be seen, the mandrel 200 may include a mandrel body 202, a mandrel cap 204, an actuation element 206 and a plurality of anti-migration feature forming pins 208. FIG. 6 is an exploded perspective view of the mandrel 200, with the anti-migration feature forming pins excluded for clarity. In some cases, the mandrel cap 204 may be releasably secured to the mandrel body 202 via a bolt 218, bayonet coupling, or other securement mechanism. In some instances, the mandrel cap 204 may be removable from the mandrel body 202 in order to facilitate removal of a stent from the mandrel 200. In other embodiments, the mandrel body 202 and the mandrel cap 204 may be formed as a unitary or monolithic structure, particularly if the mandrel cap 204 has an outer diameter roughly the same as an outer diameter of the mandrel body 202. In some instances, the mandrel body 202 may include a cylindrical portion having an outer diameter and the mandrel cap 204 may have an outer diameter greater than the cylindrical portion of the mandrel body 202.

The mandrel body 202, shown in FIGS. 5 and 6 may include a first stent shaping segment 210 and a second stent shaping segment 212. In some cases, the mandrel cap 204 may be a third stent shaping segment 211. The first stent shaping segment 210 may be a cylindrical portion of the mandrel body 202 having a first diameter the second stent shaping segment 212 may be a cylindrical portion of the mandrel body having a second diameter, and the third stent shaping segment 211 may be a cylindrical portion of the mandrel cap having a third diameter. In some cases, the first stent shaping segment 210, the second stent shaping segment 212, and/or the third stent shaping segment 211 may have a non-cylindrical profile. For example, the first stent shaping segment 210, the second stent shaping segment 212, and/or the third stent shaping segment 211 may instead have a polygonal cross-sectional profile such as an octagonal cross-sectional profile. This is just an example. The first, second and third diameters may be selected based on the desired shape of the stent in the expanded configuration. For example, the mandrel 200 illustrated in FIG. 5 may produce a stent having a generally hourglass shape. The first diameter may be different than the second diameter and/or the third diameter. For example, the first diameter may be greater than the second diameter. However, this is not required. In some cases, the first diameter and the second and/or third diameter may be the same or substantially the same. When the first and second diameter are different, a tapered segment 214 extends between the first stent shaping segment 210 and the second stent shaping segment 212 and defines a tapered surface 216 extending from a cylindrical outer surface of the first stent shaping segment 210 to a cylindrical outer surface of the second stent shaping segment 212. A similar tapered segment may extend between the second diameter and the third diameter. The tapered segment 214 includes a plurality of apertures 220 that extend through the circumferential wall of the tapered segment from the tapered surface 216 to an internal bore 228 (see, for example, FIGS. 7 and 8) extending axially within the mandrel body 202 in order to accommodate the anti-migration feature forming pins 208. It will be appreciated that an angle of the tapered surface 216, relative to the first stent shaping segment 210 and/or the second stent shaping segment 212, may influence the relative angle at which the anti-migration feature forming pins 208 extend outwardly from the tapered surface 216. In some cases, particularly if the first stent shaping segment 210, the second stent shaping segment 212, and/or the third stent shaping segment 211 have a similar or identical outer diameter, the tapered surface 216 may itself not be tapered, but may instead have a constant outer diameter.

In some instances, at least some of the plurality of apertures 220 may have a major dimension that is orthogonal to the tapered surface 216. In some cases, at least some of the plurality of apertures 220 may have a major dimension that extends at an acute angle relative to the tapered surface 216. It will be appreciated that in some cases, some of the plurality of apertures 220 may extend at different angles relative to the tapered surface 216. As shown, the plurality of apertures 220 may be considered as being radially aligned in a ring that extends around the tapered segment 214. In some cases, it will be appreciated that some of the plurality of apertures 220 may be axially displaced relative to others of the plurality of apertures 220. In other words, some of the plurality of apertures 220 may form a first ring around the tapered segment 214 while others of the plurality of apertures 220 may form a second ring around that tapered segment 214 that is axially displaced from the first ring around the tapered segment 214.

In some cases, at least some of the plurality of apertures 220 may extend linearly through the tapered segment 214 such that each corresponding pin 208 extends through the aperture 220 orthogonally to the tapered surface 216. In some cases, at least some of the apertures 220 may have a curved or helical shape, such that as the corresponding pin 208, which may have a complementary curved or helical shape, is extended out of the aperture 220, the pin 208 may rotate, and thus a distal end of the pin 208 may move radially as well as axially.

The actuation element 206 may be configured to extend into the bore 228 of the mandrel body 202 from one end of the mandrel body 202 (e.g., the end of the mandrel body opposite to the mandrel cap 204) to selectively engage and actuate the pins 208 within the apertures 220. For example, the actuation element 206, shown FIG. 6, includes a tapered end 222 that may be configured to engage the anti-migration feature forming pins 208, as well as a threaded body 224 that is configured to threadedly engage a threaded aperture extending within the first stent shaping segment 210 of the mandrel body 202. In some instances, the tapered end 222 may be conically, frustoconically, convexly, or concavely tapered. The actuation element 206 may be considered as including a handle 226 that may be used by an individual or a machine to rotate the actuation element 206 and thus advance the actuation element 206 into the bore of the mandrel body 202 by rotating in a first direction or withdraw the actuation element 206 from the bore of the mandrel body 202 by rotating in a second, opposite direction. Thus, the threaded body 224 may threadably engage a threaded region of the bore of the mandrel body 202 to threadably advance the actuation element 206 into the bore (e.g., toward the mandrel cap 204) by rotating the actuation element 206 in a first rotational direction and withdraw the actuation element 206 from the bore (e.g., away from the mandrel cap 204) by rotating the actuation element 206 in a second, opposite rotational direction. This may be demonstrated, for example, with respect to FIGS. 7 and 8, which are cross-sectional views showing the actuation element 206 fully extended into the bore 228 of the mandrel body 202 (FIG. 7) or partially extended (FIG. 8) taken along line 7-7 of FIG. 5. In other cases, it is contemplated that rather than the actuation element 206 itself including a threaded region, a threaded fastener may be configured to engage a threaded bore 228 of the mandrel body 202 to actuate the actuation element 206 relative to the mandrel body 202.

Figure 7:
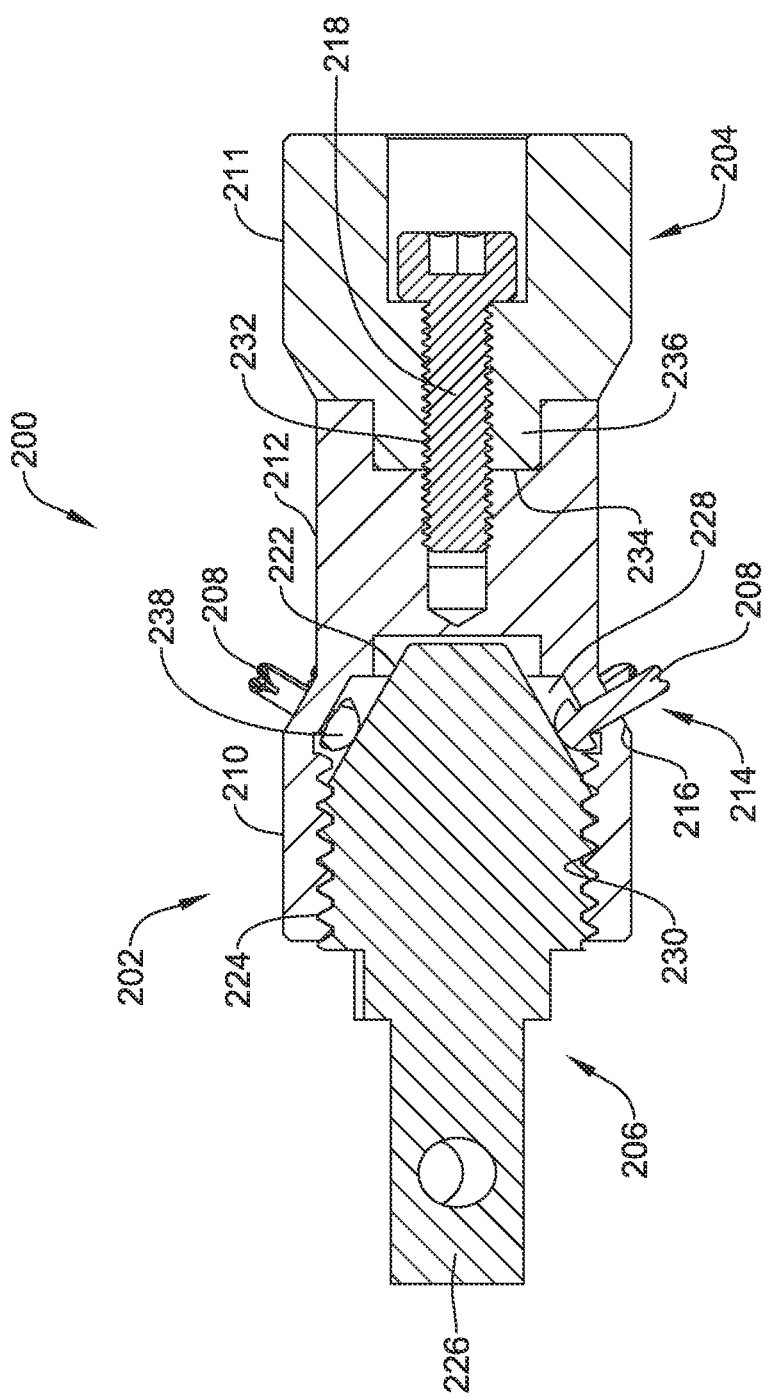
FIG. 7 is a cross-sectional view of the adjustable mandrel of FIG. 5, with the anti-migration feature forming pins shown in a fully extended position.

FIG. 7 shows the actuation element 206 fully extended into the bore 228 of the mandrel body 202 with the threaded body 224 threadably engaged with the threaded region of the bore of the mandrel body 202. In particular, the bore of the mandrel body 202 includes a first threaded region 230 extending into the first stent shaping segment 210 of the mandrel body 202 from a first end of the mandrel body 202 that is configured, in diameter, depth and thread pitch, to threadably engage the threaded body 224 of the actuation element 206. In some instances, as illustrated, the mandrel body 202 also includes a second threaded bore or region 232 extending into the second stent shaping segment 212 of the mandrel body 202 from the second, opposite end of the mandrel body that is configured, in diameter depth and thread pitch, to threadably engage threads on the threaded fastener (e.g., bolt or screw) 218 in order to releasably secure the mandrel cap 204 in position relative to the mandrel body 202 at the second end of the mandrel body 202. In some cases, it is contemplated that rather than utilizing a separate threaded fastener 218, that the mandrel cap 204 itself may include a threaded protuberance that is configured to engage the second threaded bore 232. Alternatively, it is also contemplated that the second end of the mandrel body 202 may include a threaded protuberance, and the mandrel cap 204 may include a threaded bore or aperture to engage the threaded protuberance of the mandrel body 202, or a through hole for passing the threaded protuberance through to be threadably engaged with a mating threaded fastener (e.g., nut) on an opposite side of the mandrel cap 204. In either event, the mandrel cap 204 may be secured to or removed from the mandrel body 202, particularly for aid in removing a formed stent from the mandrel 200. In some cases, the mandrel cap 204 may be permanently secured to the mandrel body 202, particularly in cases where the mandrel 200 has a profile in which an outer diameter of each successive stent shaping segment is equal to or less than an outer diameter of a preceding stent shaping segment and a formed stent may simply be slid off the mandrel 200 without removing the mandrel cap 204. In some cases, the mandrel body 202 may include a locating or centering aperture 234 that is configured to accommodate a locating or centering feature 236 extending from the mandrel cap 204, but this is not required in all cases. In some cases, rather than using the fastener 218 to secure the mandrel cap 204 to the mandrel body 202, the locating or centering feature 236 may itself threadably engage the locating or centering aperture 234.

Figure 8:
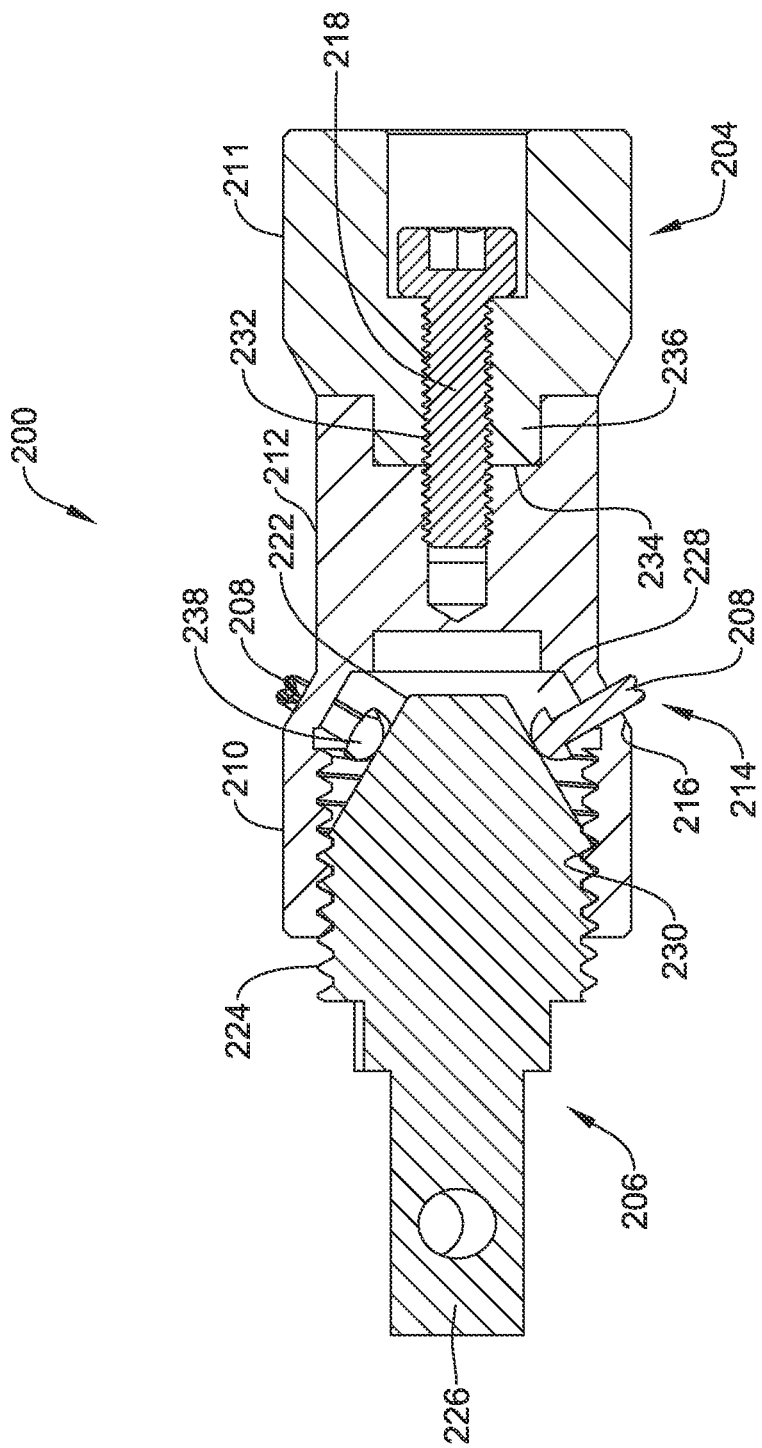
FIG. 8 is a cross-sectional view of the adjustable mandrel of FIG. 5, with the anti-migration feature forming pins shown in a partially extended position.

As shown in FIG. 7, the actuation element 206 is fully extended into the first threaded region 230 of the bore of the mandrel body 202. As a result, the anti-migration feature forming pins 208 can be seen as being extended radially outwardly through the corresponding apertures 220. In some cases, depending on the particular dimensions of the various components forming the mandrel 200, the anti-migration feature forming pins 208 may be considered as being extended radially outwardly as far as they can go before the actuation element 206 is fully extended into the first threaded region 230 of the bore of the mandrel body 202. A base 238 of each pin 208 may be seen as engaging the tapered end 222 of the actuation element 206. This can be contrasted with FIG. 8, in which the actuation element 206 is only partially extended into the first threaded region 230 of the bore of the mandrel body 202. Accordingly, while the base 238 of each pin 208 (only 2 pins are shown for clarity) is still engaged with the tapered end 222 of the actuation element 206, it can be seen that the pins 208 do not extend radially outwardly through the corresponding apertures 220 as far as the pins 208 extend in FIG. 7. In some cases, as shown in FIGS. 7 and 8, the base 238 of each pin 208 may be larger in at least one dimension than a diameter of the corresponding aperture 220. Thus, the extent that the pins 208 can be extended radially outward through the apertures 220 may be limited when the base 238 of the pin 208 abuts a peripheral edge of the aperture 220. As a result, the pins 208 are retained within the apertures 220 and won't fall out. The pins 208 can, in some instances, be removed completely by withdrawing the actuation element 206 from the bore of the mandrel body 202, permitting the pins 208 to move radially inward of the apertures 220 and then fall into the bore 228 of the mandrel body 202.

Figure 9:
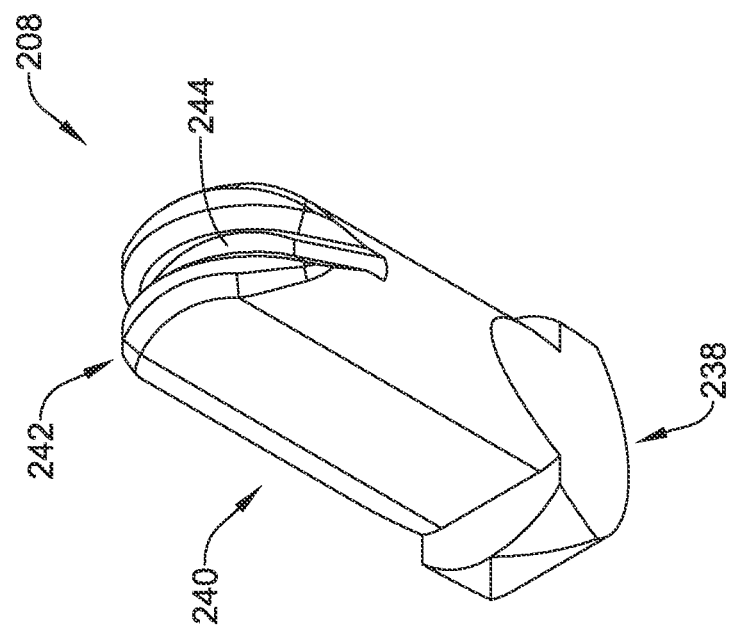
FIG. 9 is a perspective view of an anti-migration feature forming pin forming a portion of the adjustable mandrel of FIG. 5.

FIG. 9 is a perspective view of one example of an anti-migration feature forming pin 208. In some cases, the pin 208 may include a pin body 240 extending between the base 238 (which may have an enlarged cross-section relative to the pin body 240) and a pin end 242 opposite the base 238. As noted, the base 238 may be larger in diameter than the pin body 240, but this is not required in all cases. It is contemplated that the number of anti-migration forming pins 208 and the size, shape, and/or orientation (e.g., angle) thereof may be varied to achieve an anti-migration features having a desired shape and orientation. In some cases, the pin end 242 may be curved to facilitate a portion of a wire of a stent to be formed in a curved shape. In some cases, the curved shape may be a simple curve. In some instances, the curved shape may be a compound curve, such as an undulating or wave-like shape. In some instances, the pin end 242 may include a recessed slot 244 that may be configured to accommodate a wire or wires of the stent being shaped on the mandrel 200. In some cases, the recessed slot 244 may itself have a simple or compound curve shape to instill a corresponding simple or compound curve shape to a stent wire extending through the recessed slot 244. For example, in some embodiments the recessed slot 244 may be a curved slot 244 providing a wire placed therein with a curved region. In some cases the recessed slot 244 may include two converging portions converging at a point at the pin end 242 to provide a wire with a sharp bend for an anti-migration feature. In some cases, the stent being formed is a knitted stent, and a constant diameter knitted stent blank, such as stent 10 or 100, may be stretched over the mandrel 200, with a particular wire of the knitted stent blank disposed within the recessed curved slot 244 in order to form an anti-migration feature extending radially outward from a knitted tubular wall of the stent. In other cases, the stent may be knitted directly over the mandrel 200.

While the pin end 242 is illustrated as a curved profile and being no larger in dimension than the pin body 240, in some cases it is contemplated that the pin end 242 may extend laterally beyond the pin body 240 and form an arcuate surface. In some cases, for example, the arcuate surface of each of the pin ends 242 may align end to end, and essentially form a raised ring extending around the mandrel 200. The individual arcuate surfaces of each of the pin ends 242 may be driven outward by extending the actuation element 206 into the mandrel body 202 by rotating the actuation element 206 in a first rotational direction in order to form a raised ring anti-migration feature in the stent.

Rotating the actuation element 206 in a second, opposing rotational direction, allows the pins 208 to retract, and allow removal of the stent from the mandrel 200.

Figure 10:
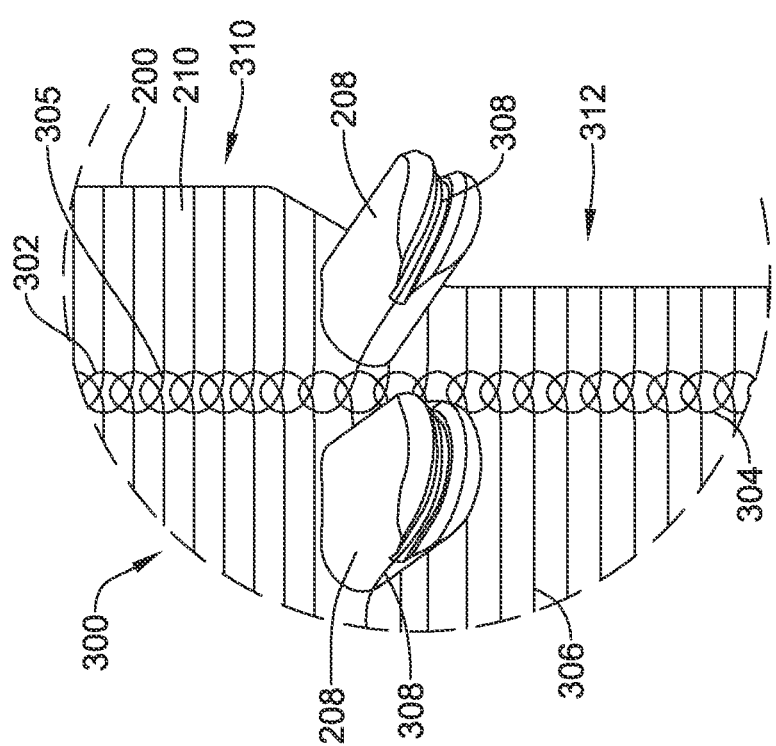
FIG. 10 is a side view of a portion of the adjustable mandrel of FIG. 5, showing a portion of a knitted stent disposed about the adjustable mandrel.
Figure 11A:
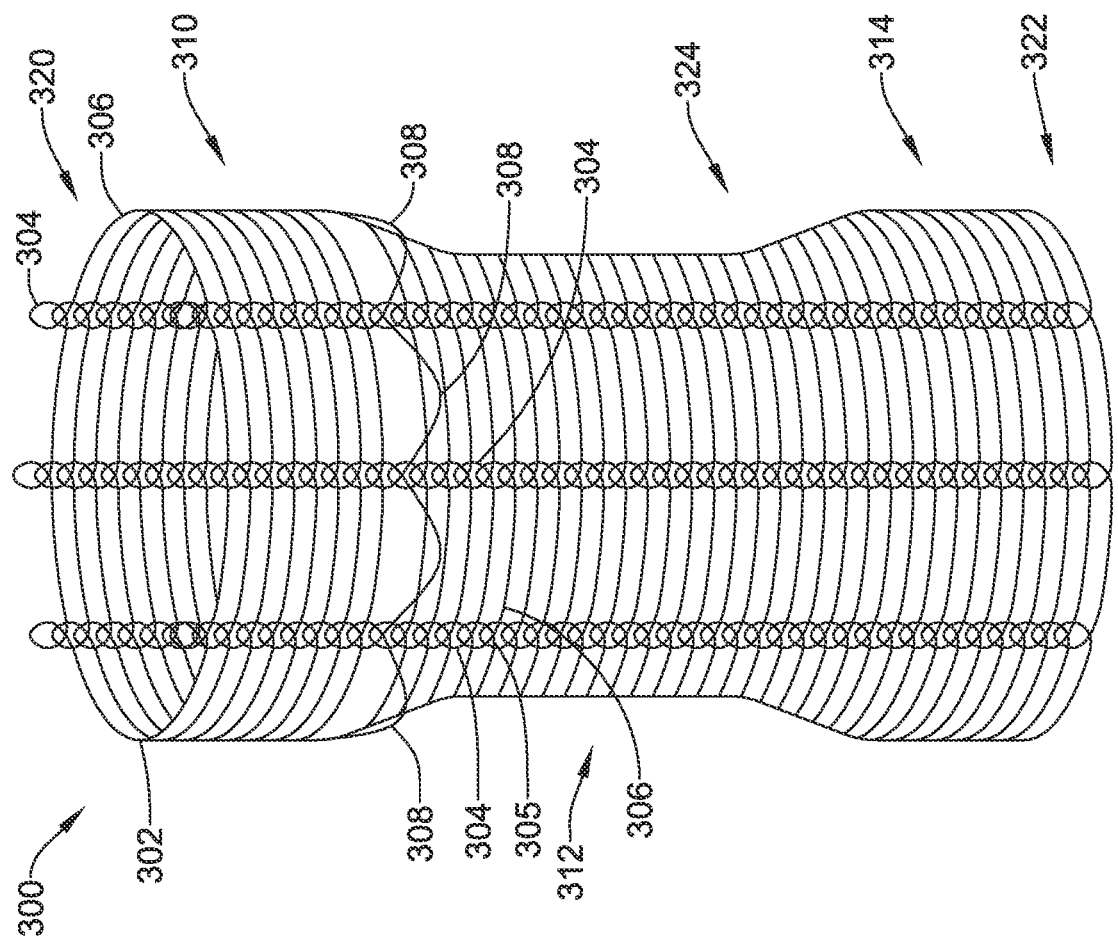
FIG. 11A is a side view of the illustrative knitted stent of FIG. 10 removed from the adjustable mandrel.

FIG. 10 shows a portion of a knitted stent 300 disposed on the mandrel 200, while FIG. 11A shows the knitted stent 300 removed from the mandrel 200. The stent 300 may be similar in form and function to the stents 10, 100 described above. The stent 300 may have a first, or proximal end 320, a second, or distal end 322, and an intermediate region 324 disposed between the first end 320 and the second end 322. Generally, the stent 300 may be formed from a single knitted strand or filament 302, as described above with respect to stents 10, 100. The stent 300 includes a plurality of loops 304 each with an overlapping base portion 305 and a plurality of interconnecting rung sections 306. As shown in FIG. 10, one of the rung sections 306 of the knitted stent 300 may extend radially outward from the knitted tubular wall of the stent 300 and along the recessed slot 244 of the pin 208 to form one or more of the anti-migration features 308 of the stent 300. Thus, the outwardly extending rung section 306 forming the anti-migration feature 308 may extend radially outward relative to rung sections 306 longitudinally and/or circumferentially adjacent thereto. In some cases, a knitted stent such as the knitted stent 300 may be formed by first knitting a constant diameter stent blank (not illustrated), then stretching the constant diameter stent blank over the mandrel 200 prior to a shaping process and/or an annealing process. It can be seen that the knitted stent 300 has a first enlarged diameter portion 310 proximate a first end of the knitted stent 300 that corresponds to the first stent shaping segment 210, a second enlarged diameter portion 314 proximate a second end of the knitted stent 300 that corresponds to the third stent shaping segment 211, and a (relatively) reduced diameter portion 312 (e.g., a cylindrical body region intermediate the first and second enlarged diameter portions 310, 314) that corresponds to the second stent shaping segment 212.

Figure 11B:
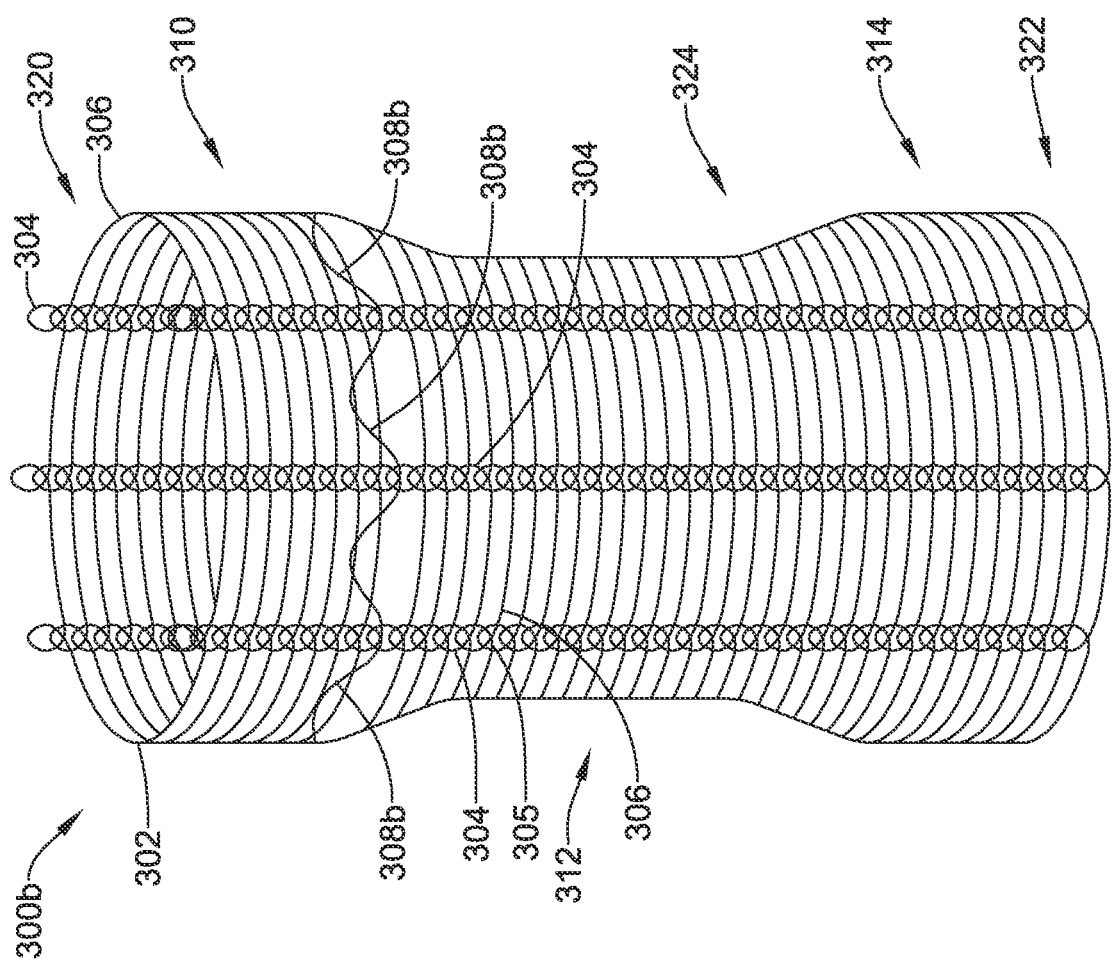
FIG. 11B is a side view of another illustrative knitted stent removed from the adjustable mandrel.
Figure 11C:
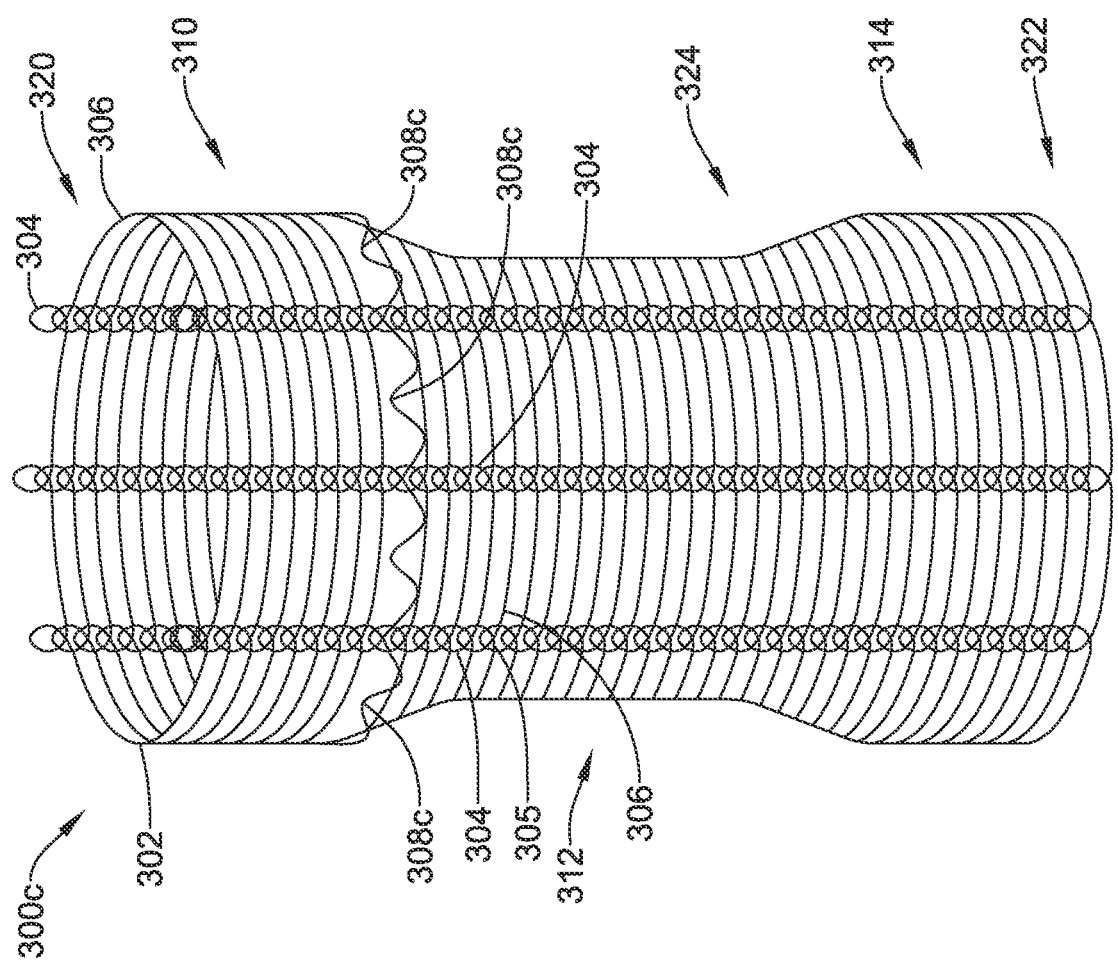
FIG. 11C is a side view of another illustrative knitted stent removed from the adjustable mandrel.

The knitted stent 300 includes anti-migration features 308 that correspond to the pins 208 which are arranged circumferentially around the knitted stent 300 at a transition region between the first enlarged dimeter portion 310 and the reduced diameter portion 312. However, it is contemplated that the anti-migration features 308 may be arranged at a different location along the length of the knitted stent 300, if desired. The pins 208 may be actuated radially outward with the wires disposed in the recessed slots 244 after the knitted stent black has been placed on the mandrel 200 to cause the portions of the wires engaged with the pins 208 to be urged radially outward from the knitted tubular wall of the stent to form the anti-migration features 308. The anti-migration features 308 may extend in a generally distal direction. However, this is not required. It is contemplated that the general orientation of the anti-migration features 308 can be changed as desired by changing an orientation or shape of the pins 208. For example, FIG. 11B illustrates a perspective view of an illustrative stent 300b having an alternative configuration for the anti-migration features 308b. In the illustrative embodiment of FIG. 11B, the anti-migration features 308b are oriented in a generally proximal direction. FIG. 11C illustrates a perspective view an illustrative stent 300c having yet another alternative configuration for the anti-migration features 308c. In the illustrative embodiment of FIG. 11C, the anti-migration features 308c initially extend in a generally distal direction and are then turned back on themselves such that an apex of the anti-migration features 308c is pointed in a more proximal direction. Other orientations or combinations of orientations may be used, as desired.

FIG. 12A is an end view of the knitted stent 300, showing the anti-migration features 308 extending radially outward from the knitted tubular wall of the knitted stent 300. As illustrated, each of the anti-migration features 308 are loops of the filament(s) or wire(s) forming the knitted stent 300 extending between adjacent overlapping base portions 305, each loop being roughly equal in shape and dimension. As described above, overlapping base portions 305 may be the location in which portions of the filament(s) or wire(s) cross or loop around another portion of the filament(s) or wire(s). In other cases, some of the anti-migration features 308 may vary in shape and/or dimension, or may not be equally spaced, for example. While the anti-migration features 308 are shown as being curved, in some cases the anti-migration features 308 may be pointed, or include a flattened region, for example.

Figure 12B:
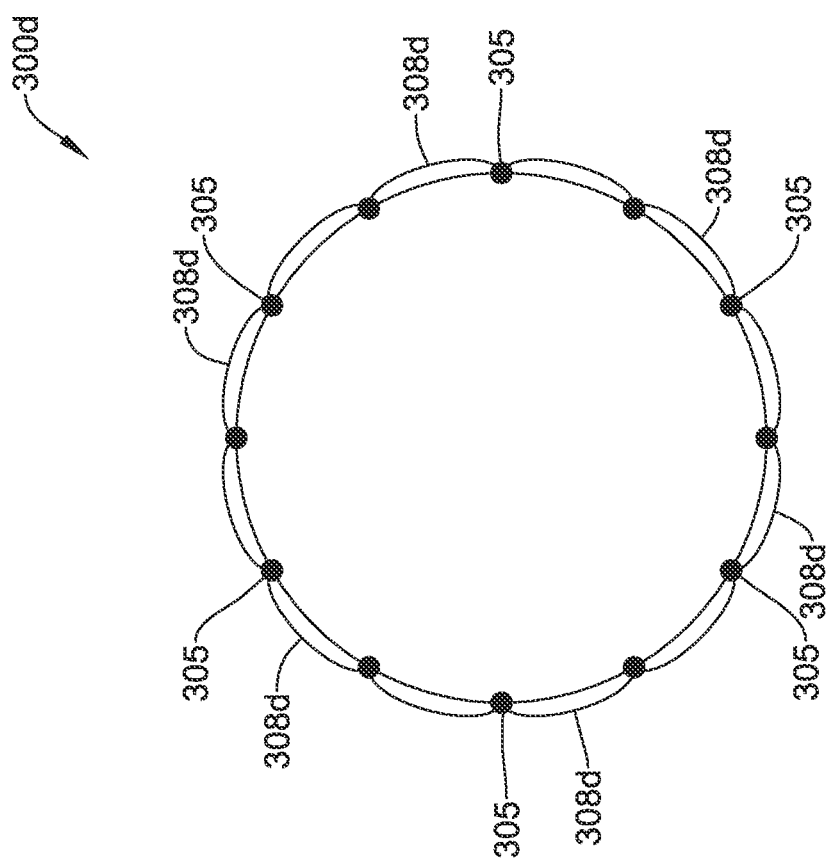

FIG. 12B, for example, shows a knitted stent 300d that includes a number of anti-migration features 308d. The anti-migration features 308d each extend between adjacent overlapping base portions 305, and are each roughly equal in shape and dimension. However, by comparing FIG. 12B with FIG. 12A, it can be seen that the anti-migration features 308 shown in FIG. 12A extend radially outward further than the anti-migration features 308d shown in FIG. 12B. The anti-migration features 308d may be formed, for example, by using anti-migration feature forming pins 208 that are shorter in length, or by not advancing the actuation element 206 as far into the mandrel body 202, thus not advancing the pins 208 radially outward as far from the surface of the tapered segment 214 of the mandrel body 202. The anti-migration features 308d may be pointed, for example, or have other shapes as well.

It will be appreciated that the relative dimensions of the anti-migration features 308 and the anti-migration features 308d may be a function of the ultimate end-use of the knitted stent 300 (or 300d). Relatively larger anti-migration features 308, 308d may be useful in situations where the knitted stent 300 (or 300d) will be placed in anatomical locations where the knitted stent 300 (or 300d) may be subjected to relatively stronger migration forces and/or anatomical locations where the dimensions of the patient's anatomy are more variable. Relatively smaller anti-migration features 308, 308d may be useful in situations where the knitted stent 300 (or 300d) may be subjected to relatively weaker migration forces and/or anatomical locations where the dimensions of the patient's anatomy are less variable. In some cases, the overall dimensions of the knitted stent 300 (or 300d) may play a part as well. In some cases, for example, a larger diameter knitted stent 300 (or 300d) may have relatively larger anti-migration features 308, 308d while a smaller diameter knitted stent 300 (or 300d) may have relatively smaller anti-migration features 308, 308d.

Figure 12C:
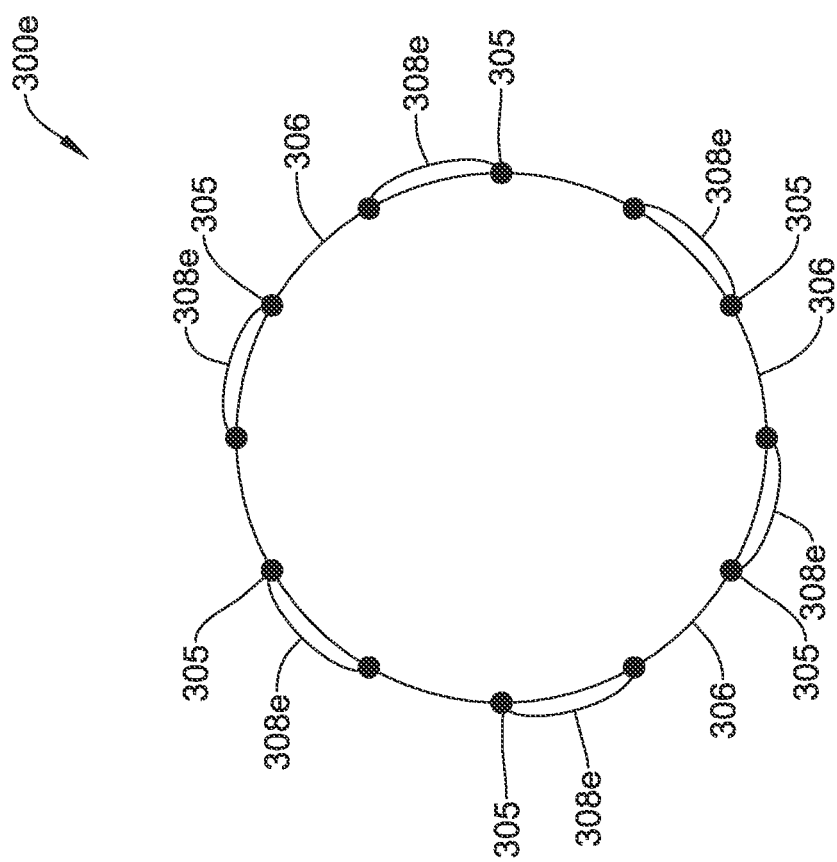

FIG. 12C shows a knitted stent 300e that includes a number of anti-migration features 308e. In contrast to the knitted stents 300 and 300d shown in FIGS. 12A and 12B, the anti-migration features 308e do not extend between each adjacent overlapping base portion 305 about the periphery of the knitted stent 308b. Each of the anti-migration features 308e extends between adjacent overlapping base portion 305, although some overlapping base portion 305 are not attached to an anti-migration feature 308e. The anti-migration features 308e illustrated in FIG. 12C may have an alternating pattern (e.g., alternating between an anti-migration features 308e and a rung section 306). Other patterns or asymmetric arrangements can be used as desired. As illustrated, each of the anti-migration features 308e are roughly equal in shape and dimension. The anti-migration features 308e may be formed, for example, by only placing anti-migration feature forming pins 208 into some of the apertures 220. In some cases, it is contemplated that some of the anti-migration features 308e may be smaller or larger in dimension, and/or may vary in shape, relative to others of the anti-migration features 308e.

Figure 12D:
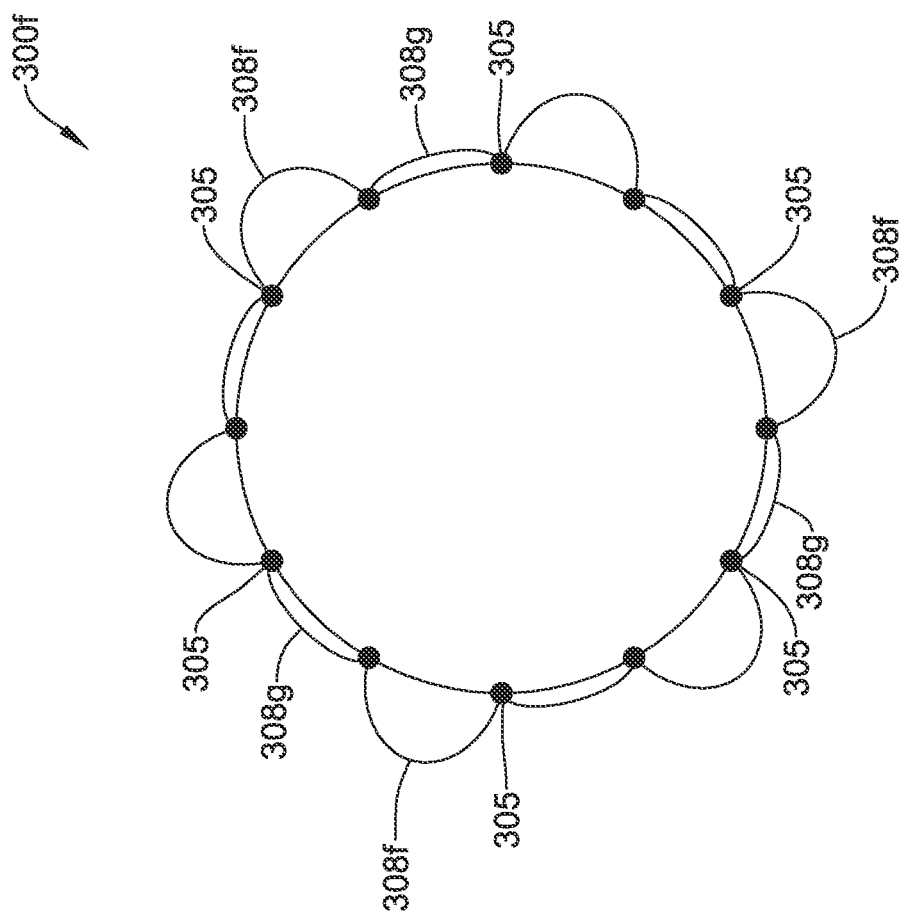

FIG. 12D shows a knitted stent 300f that includes a number of anti-migration features 308f and a number of anti-migration features 308g, each extending between adjacent overlapping base portions 305. It will be appreciated that as illustrated, each of the anti-migration features 308f are roughly equal in shape and dimension, and each of the anti-migration features 308g are roughly equal in shape and dimension, albeit not extending radially outward as far as the anti-migration features 308g. The anti-migration features 308f and 308g may be formed, for example, by using a longer length pin 208 to form each of the anti-migration features 308f and a shorter length pin 208 to form each of the anti-migration features 308g. It will be appreciated that the particular anti-migration features 308, 308b, 308c, 308d, 308e, 308f, and 308g shown in FIGS. 11A-11C and 12A-12D are merely illustrative, and may be mixed or matched in any desired pattern.

Figure 13:
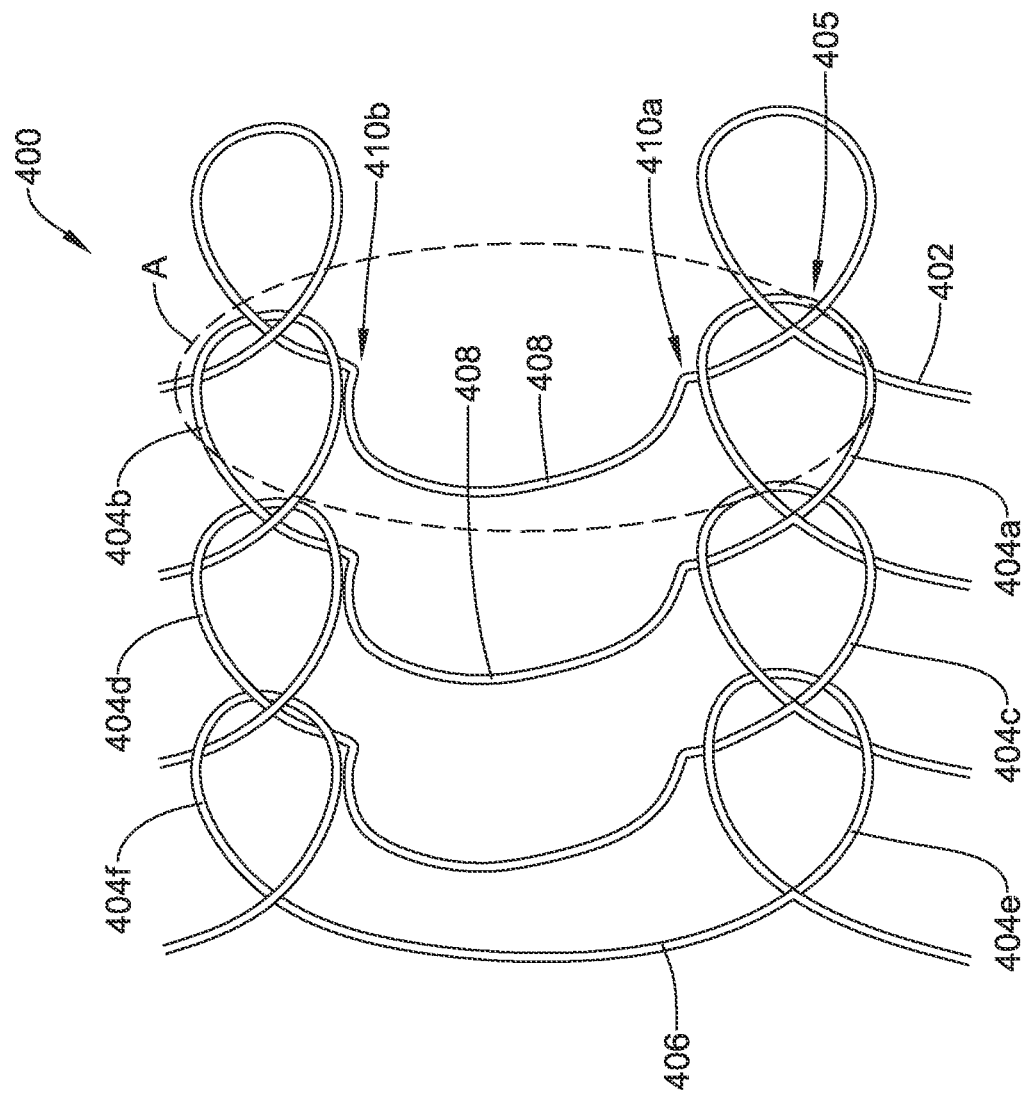
FIG. 13 is a partial side view of another illustrative knitted stent having one or more anti-migration features.

FIG. 13 is a partial side view of another knitted stent 400 having one or more anti-migration features 408. The stent 400 may be similar in form and function to any of the stents described herein. For example, the stent 400 may have a generally constant diameter from a proximal end to a distal end similar to the stents 10, 100 described above. Alternatively, the stent 400 may include one or more regions having an increased diameter similar to the stent 300 described above. The stent 400 may be formed from a single knitted strand or filament 402. The strand 402 may be manipulated (e.g., knitted) into a plurality of rows each having a plurality of interconnected or intermeshing loops 404a-f (collectively, 404) each with an overlapping base portion 405. The stent 400 may include as many rows as required to form a stent 400 having the desired length. As described above, the loops 404 may be loosely knit and include interconnecting intermediate rung portions 406 between the loops 404. It is further contemplated that the stent 400 need not be formed from a single strand 402 but rather may include two or more strands knitted together. In some instances, a loop may be generally aligned with, or suspended from, a loop of the preceding row in a direction generally parallel to a longitudinal axis of the stent 400 (for example, circumferentially aligned along a length of the stent 100). Thus, the loops 404 may form axially extending columns or wales, although this is not required.

As described above, some (or all) of the intermediate rung portions 406 may be formed into anti-migration features 408. For example, one or more rung portions 406 may be biased to radially extend from the main body of the stent 400 using a mandrel, such as the mandrel 200 described herein. It is contemplated that while the anti-migration features 408 are being formed, a point bend 410a, 410b (collectively, 410) may be formed in one or more of the anti-migration features 408. The point bends 410 may be a pinch point or a region where the anti-migration features 408 undergo an abrupt change in direct as opposed to a smooth curve. The point bends 410 may be formed near or at the intersection of the anti-migration features 408 with the adjacent loop 404a, 404b when the stent is in a radially expanded configuration. The portion of the strand 402 forming the anti-migration features 408 and including the point bends 410 may pass under the adjacent loop 404a, 404b to tie the anti-migration feature 408 back into the stent 400. It is contemplated that the angle of the point bends 410 may be selected to provide a desired angle or orientation of the anti-migration features 408. The point bends 410 may be formed using anti-migration feature forming pins 208. For example, the pins 208 may include a recess along a lower edge thereof to form the point bend. The stent 400 may be annealed or heat treated after formation of the anti-migration features 408 and/or point bends 410.

Figure 14:
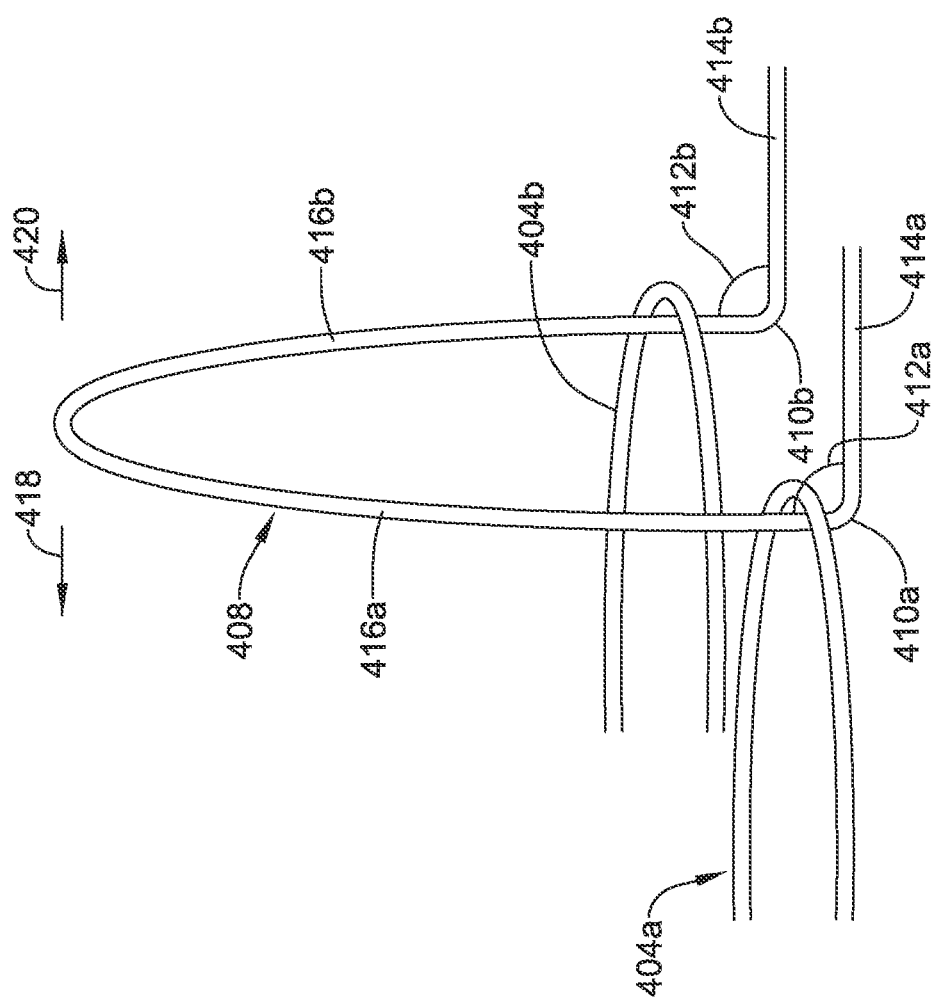
FIG. 14 is a side view of region A of the stent of FIG. 13.

When the stent 400 is deployed, the anti-migration features 408 radially protrude from the stent 400, as shown in FIG. 14, which illustrates a side view of region A of the stent 400 of FIG. 13. As can be seen in FIG. 14, the point bends 410 may be positioned underneath or adjacent to the loops 404a, 404b in the radially expanded configuration. While the anti-migration feature 408 is illustrated as extending generally orthogonal to longitudinal axis of the stent 400, the anti-migration features 408 may extend at an angle between about 0° and 180° relative to the longitudinal axis of the stent 400. The point bends 410 may be formed between a first portion or arm 414a, 414b (collectively, 414) of the filament and a second portion or arm 416a, 416b (collectively, 416). The first arms 414 may be a portion of the filament exiting the adjacent loops 404 while the second arms 416 may together form the anti-migration features 408. The point bends 410 may be formed such that the second portion 416 extends at an angle 412a, 412b (collectively, 412) relative to the first portion 414. The angle 412 may determine the angle and/or direction the anti-migration features 408 are oriented. For example, in the illustrated example, the angle 412 is around 90° and thus the anti-migration features 408 extend at an angle of about 90° relative to the longitudinal axis of the stent 400. If the point bends 410 are formed such that the angle 412 is obtuse, the anti-migration features 408 may be pointed in a generally distal direction 418. For example, in some instances the angle 412 may be greater than 90° but less than 155°, greater than 90° but less than 145°, greater than 90° but less than 135°, greater than 90° but less than 120°, greater than 100° but less than 155°, greater than 100° but less than 145°, greater than 100° but less than 135°, or greater than 100° but less than 120°. If the point bends 410 are formed such that the angle 412 is acute, the anti-migration features 408 may be pointed in a generally proximal direction 420. For example, in some instances the angle 412 may be less than 90° but greater than 25°, less than 90° but greater than 35°, less than 90° but greater than 45°, less than 90° but greater than 55°, less than 80° but greater than 25°, less than 80° but greater than 35°, less than 80° but greater than 45°, or less than 80° but greater than 55°.

It is contemplated the angle 410 may be determined by a radius of curvature of the point bends 410. A smaller radius of curvature may result in a sharper angle 412 while a larger radius of curvature may result in a less sharp angle 412. In some instances, the radius of curvature of the angle 412 may be less than four times the diameter of the strand or filament, may be less than three times the diameter of the strand or filament, may be less than two times the diameter of the strand or filament, or the radius of curvature of the angle 412 may be less than or equal to the diameter of the strand or filament. In some embodiments, the point bends 410 may be formed to have similar angles 412 (and/or radii of curvature). In other embodiments, some anti-migration features 408 may be formed with a first angle 412 and other anti-migration features 408 may be formed with a second angle, different from the first 412. This may allow the anti-migration features 408 to have differing radial profiles (as shown in FIG. 12D). It is contemplated that any number of angles 412 may be combined in varying patterns to achieve the desired effect.

Figure 15:
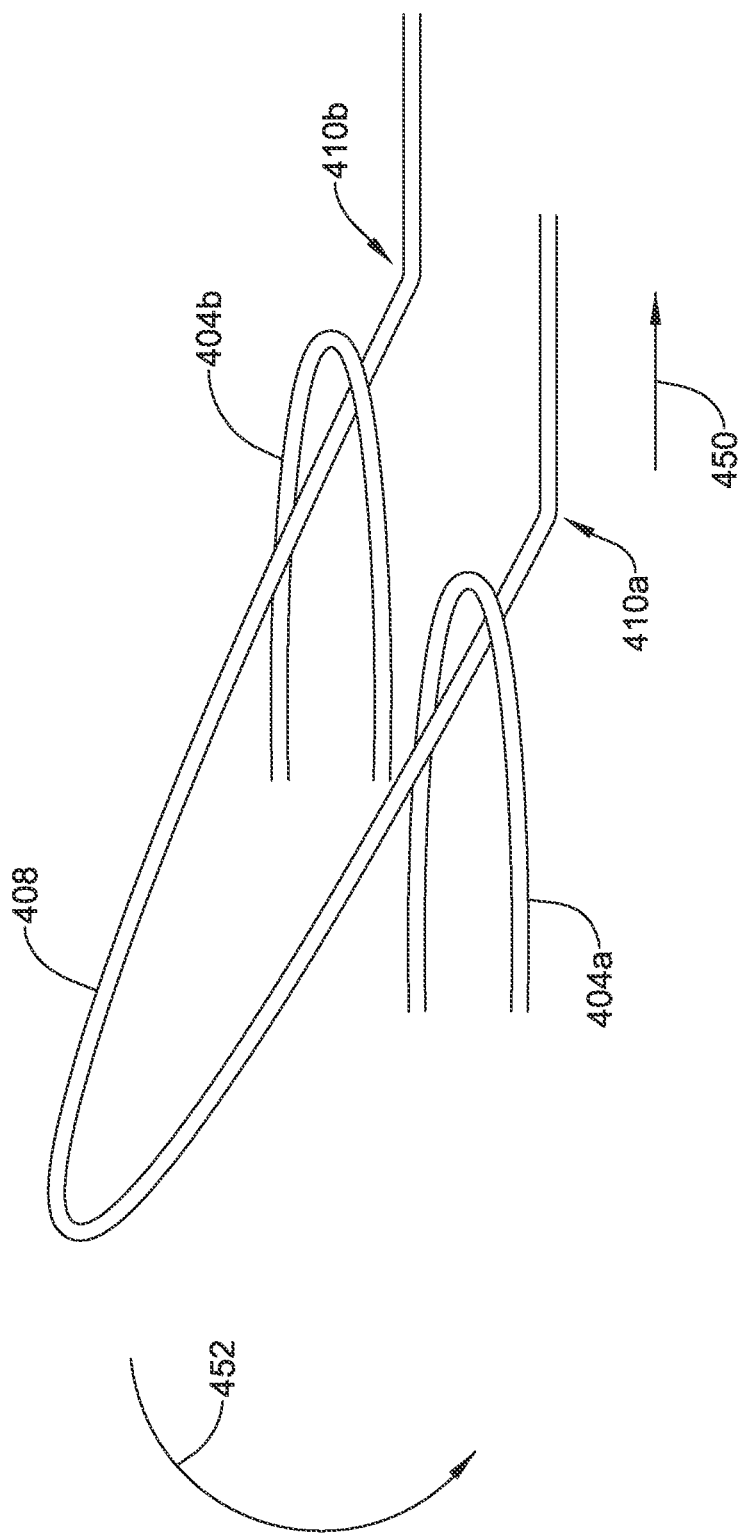
FIG. 15 is a side view of the stent of FIG. 14 in a second configuration.

Referring additionally to FIG. 15, which illustrates the stent 400 of FIG. 14 under an applied force 450, when a removal force is applied to the stent 400, for repositioning or removal of the stent 400, the stent 400 may begin to elongate (in a similar manner to that show in FIG. 3). As the stent 400 elongates, the point bends 410 are pulled through the adjacent loops 404a, 404b. As the point bends 410 are passed through the loops 404, the anti-migration feature 408 is deflected radially inward, as shown at arrow 452, to lie flat along the body of the stent 400. Thus, a portion of the anti-migration feature 408 (portions of the strand or filament forming the anti-migration feature 408 between adjacent point pends 410, may also be pulled through the adjacent loops 404a, 404b. In some instances, as the stent 400 elongates, the angle 412 at the point bend 410 may increase as the anti-migration feature 408 is deflected radially inward toward the outer dimeter of the body of the stent 400. It is contemplated that each anti-migration feature 408 that is positioned at a similar longitudinal location along the stent 10 may deflect down at a same point of elongation of the stent 10. These features may reduce the force required to move or remove the stent 400 from the body or tissue. It is contemplated that the direction of the applied force may vary based on the direction in which the anti-migration features 408 are oriented and/or an angle of the point bends 410. For example, distally oriented anti-migration features 408 may be more readily disengaged from the tissue with a proximally applied force while proximally oriented anti-migration features 408 may be more readily disengaged from the tissue with a distally applied force.

To form a knitted stent, such as the stents 10, 100, 300, 300b-f, 400 described herein having a non-uniform profile and one or more anti-migration features, a constant diameter knitted stent blank (as shown in FIG. 4) may be positioned over a mandrel (such as mandrel 200) having a tapered outer surface and one or more anti-migration feature forming elements. It should be noted that a knitted stent having a generally uniform diameter and one or more anti-migration features can be formed by place a constant diameter knitted stent blank over a generally uniform mandrel with one or more anti-migration feature forming elements. In other embodiments, a knitted stent having a non-uniform or a uniform profile may be knitted directly over the mandrel having one or more anti-migration feature forming elements. In some cases, disposing a constant diameter knitted stent blank in position over a mandrel includes stretching the constant diameter knitted stent blank over the mandrel and allowing the constant diameter knitted stent blank to conform to the varied diameter outer surface of the mandrel (e.g., conforming to the various constant diameter regions and/or tapered diameter regions of the mandrel).

The one or more anti-migration feature forming elements (such as but not limited to the pins 208) may be engaged by a portion of the stent in order to provide a desired shape prior to annealing. In some cases, the one or more anti-migration feature forming elements are pins that are configured to be driven in a radially outward direction relative to the outer surface of the mandrel. Engaging the one or more anti-migration feature forming elements with the stent may include driving the pins in radially outward direction relative to the mandrel to urge the wire(s) or filament(s) engaged with the end of each of the pins in a radially outward direction relative to the knitted tubular structure of the stent.

The mandrel and the stent thereon, with the anti-migration features formed, may then be subjected to an annealing or shape setting process. After the annealing or shape setting process, the one or more anti-migration feature forming elements may be disengaged in order to remove the shaped stent from the mandrel. In some cases, disengaging the one or more anti-migration feature forming elements comprises permitting the pins to move in an inward direction relative to the mandrel.

In some cases, it may be desirable to form knitted stent with one or more anti-migration features from a metallic component and a non-metallic or even biodegradable component. In such a case, the metallic component and the non-metallic component may individually be shaped, and then combined to form a stent. In some cases, each of the metallic component and the non-metallic or even biodegradable component may each include anti-migration features, where the anti-migration features of the non-metallic or even biodegradable component complement the anti-migration features of the metallic component. In cases where the non-metallic component is biodegradable, the biodegradable anti-migration features may provide additional resistance to migration upon initial implantation of the stent, but dissolve away over time.

To form a two (or more) component stent, in some cases, a constant diameter metallic knitted stent blank may be positioned over a mandrel having a tapered outer surface and one or more anti-migration feature forming elements. The mandrel may be the mandrel 200, for example. However, it is not required for the mandrel to have tapered surfaces or varying diameters. In some cases, disposing a constant diameter metallic knitted stent blank in position over a mandrel includes stretching the constant diameter metallic knitted stent blank over the mandrel and allowing the constant diameter metallic knitted stent blank to conform to the varied diameter outer surface of the mandrel (e.g., conforming to the various constant diameter regions and/or tapered diameter regions of the mandrel).

The one or more anti-migration feature forming elements (such as but not limited to the pins 208) may be engaged with a portion of the metallic knitted stent in order to provide a desired shape prior to annealing. In some cases, the one or more anti-migration feature forming elements are pins that are configured to be driven in a radially outward direction relative to the outer surface of the mandrel. For example, to engage a portion of the stent the pins are driven in radially outward direction relative to the mandrel to urge the wire(s) or filament(s) engaged with the end of each of the pins in a radially outward direction relative to the knitted tubular structure of the stent. The mandrel and the stent thereon, with the anti-migration features formed, may then be subjected to an annealing or shape setting process. After the annealing or shape setting process, the one or more anti-migration feature forming elements may be disengaged in order to remove the shaped stent from the mandrel. In some cases, disengaging the one or more anti-migration feature forming elements comprises permitting the pins to move in an inward direction relative to the mandrel.

In some cases, once the shaped metallic stent has been removed from the mandrel, a constant diameter biodegradable knitted stent blank may be positioned over a mandrel having a tapered outer surface and one or more anti-migration feature forming elements. In some cases, disposing a constant diameter biodegradable knitted stent blank in position over a mandrel includes stretching the constant diameter biodegradable knitted stent blank over the mandrel and allowing the constant diameter biodegradable knitted stent blank to conform to the varied diameter outer surface of the mandrel. The one or more anti-migration feature forming elements may be engaged in order to provide a desired shape prior to annealing.

In some cases, the annealing process for the biodegradable knitted stent blank may involve lower temperatures than that used for the metallic knitted stent blank. The mandrel and the stent thereon, with the anti-migration features formed, may then be subjected to an annealing or shape setting process. After the annealing or shape setting process, the one or more anti-migration feature forming elements may be disengaged in order to remove the shaped biodegradable stent from the mandrel. In some cases, disengaging the one or more anti-migration feature forming elements comprises permitting the pins to move in an inward direction relative to the mandrel. In some cases, while not illustrated, the shaped biodegradable stent may be disposed about or within the shaped metallic stent.

Figure 16:
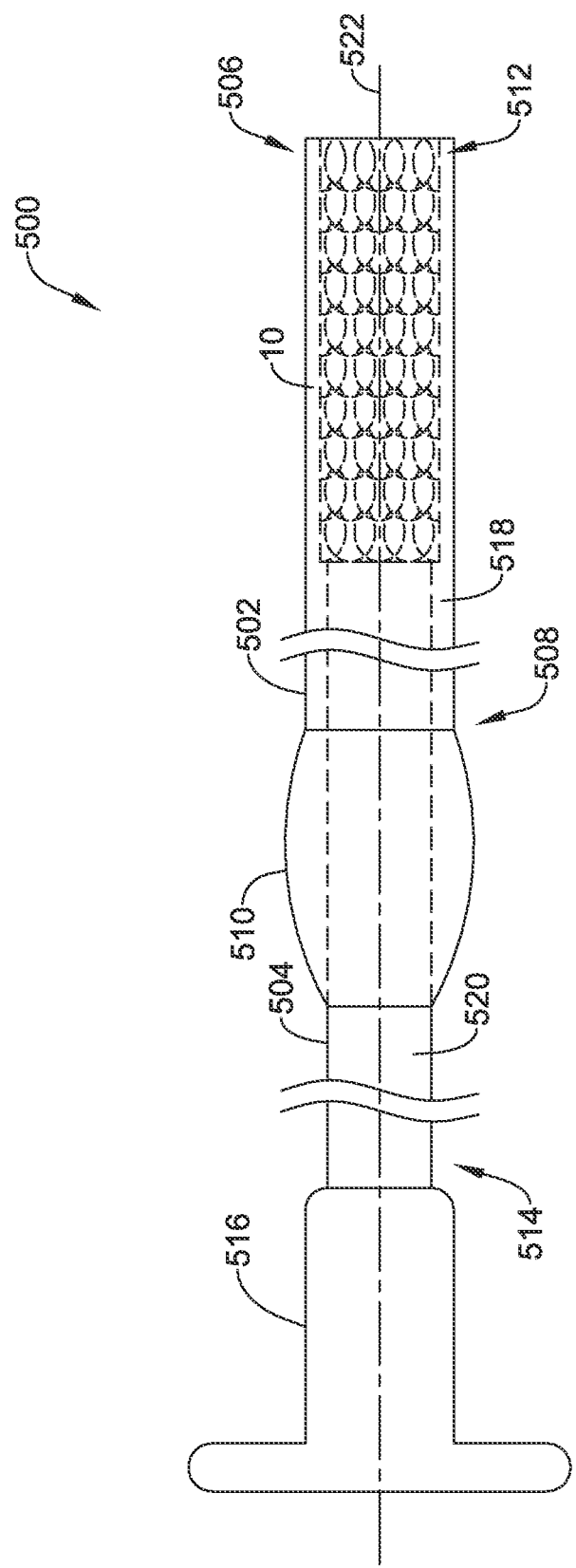
FIG. 16 is a side view of an illustrative delivery system for delivering a stent.

FIG. 16 is a side view of an illustrative delivery system 500 for delivering a stent, such as the stents 10, 100, 300, 300b-f, 400 described herein, to a target region. The delivery system 500 may include an outer or exterior elongate shaft or tubular member 502 and an inner elongate shaft or tubular member 504. The inner tubular member 504 may be slidably disposed within a lumen of the outer tubular member 502. The outer tubular member 502 may extend proximally from a distal end region 506 to a proximal end region 508 configured to remain outside of a patient's body. A first hub or handle 510 may be coupled to the proximal end region 508 of the outer tubular member 502. The inner tubular member 504 may extend proximally from a distal end region 512 to a proximal end region 514 configured to remain outside of a patient's body. A second hub or handle 516 may be coupled to the proximal end region 514 of the inner tubular member 504. In some instances, the distal end region 506 of the outer tubular member 502 may be configured to be atraumatic.

The outer tubular member 502 may include a lumen 518 extending from the distal end region 506 to the proximal end region 508. The lumen 518 may also extend through the first handle 510. The lumen 518 of the outer shaft 502 and the first handle 510 may be configured to slidably receive the inner shaft 504. The inner tubular member 504 may include a lumen 520 extending from the distal end region 512 to the proximal end region 514. The lumen 520 of the inner tubular shaft 504 may also extend through the second handle 516. The lumen 520 of the inner shaft 504 may be configured to receive a guidewire 522, as desired.

The stent 10 may be disposed around a portion of the inner tubular member 504 at or adjacent to the distal end region 512 thereof. When the stent 10 is disposed over the inner tubular member 504, in a collapsed and elongated delivery configuration, the stent 10 may be restrained in a collapsed reduced diameter or delivery configuration by the outer tubular member 502 surrounding the stent 10. In the collapsed configuration, the stent 10 may have a smaller diameter and a longer length than the expanded deployed configuration. The distal end region 506 of the outer tubular member 502 may be positioned such that the outer tubular member 502 surrounds and covers the length of the stent 10 during delivery. The outer tubular member 502 may have sufficient hoop strength to retain the stent 10 in its reduced diameter state.

Figure 17:
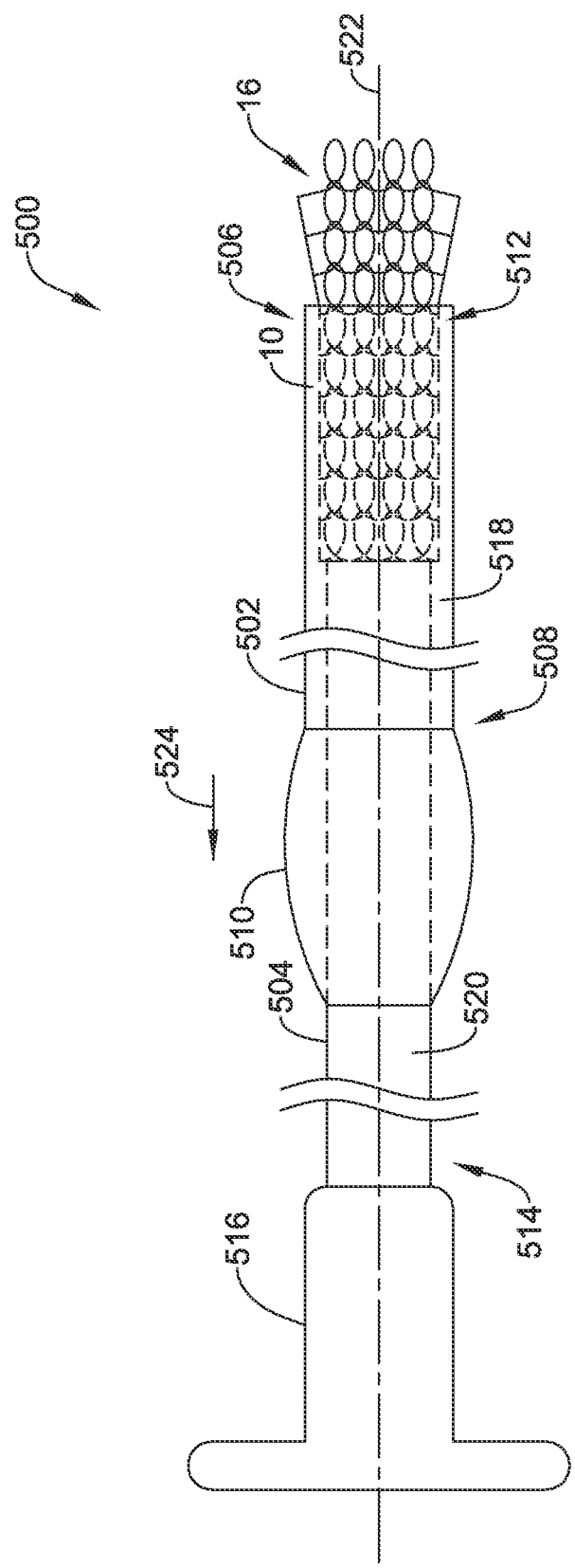
FIG. 17 is a side view of the illustrative delivery system of FIG. 16 with the stent in a partially deployed configuration.

FIG. 17 illustrates a side view of the delivery system 500 with the stent 10 in a partially deployed configuration. The delivery system 500 may be advanced through the gastrointestinal tract (or other body lumen), as desired. The delivery system 500 may be advanced with or without the use of a guidewire 522. Once the stent 10 is positioned adjacent to the target region, the restraining forces maintaining the stent 10 in the radially collapsed configuration may be removed to deploy the stent 10.

The stent 10 may be released by actuating the first handle 510 proximally relative to the second handle 516, e.g., by pulling the first handle 510 proximally 524 while maintaining the second handle 516 in a fixed position. Thus, the outer tubular shaft 502 may be retracted proximally relative to the inner tubular shaft 504. In other words, the outer tubular shaft 502 may be proximally retracted while the inner tubular shaft 504 is held stationary. As shown in FIG. 17, as the outer tubular shaft 502 is retracted proximally 524 to uncover the stent 10, the biasing force is removed from the exterior of the stent 10 and the stent 10 assumes its radially expanded, unbiased, deployed configuration. Once the outer tubular member 502 no longer covers the proximal end 14 of the stent 10, the stent 10 may assume its fully deployed configuration, as shown in FIG. 1. The delivery system 500 may then be removed from the body lumen.

The stents, delivery systems, and the various components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic Nitinol; other nickel alloys such as nickel-chromium-molybdenum alloys, nickel-copper alloys, nickel-cobalt-chromium-molybdenum alloys, nickel-molybdenum alloys, other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys; platinum enriched stainless steel; titanium; combinations thereof; and the like; or any other suitable material.

Some examples of suitable polymers for the stents or delivery systems may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX®low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styreneb-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

In at least some embodiments, portions or all of the stents or delivery systems may also be doped with, made of, or otherwise include a radiopaque material. Radiopaque materials are generally understood to be materials which are opaque to RF energy in the wavelength range spanning x-ray to gamma-ray (at thicknesses of <0.005"). These materials are capable of producing a relatively dark image on a fluoroscopy screen relative to the light image that non-radiopaque materials such as tissue produce. This relatively bright image aids the user of the stents or delivery systems in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the stents or delivery systems to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A stent, the stent comprising:
an elongated tubular member comprising at least one knitted filament having a plurality of twisted knit stitches with intermediate rung portions extending between adjacent twisted knit stitches, the elongated tubular member configured to move between a collapsed configuration and an expanded configuration; and
one or more anti-migration features formed in one or more of the intermediate rung portions;
wherein when the elongated tubular member is in the expanded configuration, the one or more anti-migration features extend radially therefrom; and
wherein the one or more anti-migration features each includes a first joint bend adjacent a first twisted knit stitch and a second joint bend adjacent a second twisted knit stitch.

2. The stent of claim 1, wherein the one or more anti-migration features extend in the range of 1 to 4 millimeters radially beyond a base diameter of the elongated tubular member in the expanded configuration.

3. The stent of claim 1, wherein when the elongated tubular member is in the expanded configuration the one or more anti-migration features extend at a non-parallel angle relative to a longitudinal axis of the elongated tubular body.

4. The stent of claim 1, wherein when the elongated tubular member is in the expanded configuration the one or more anti-migration features include a distally oriented apex.

5. The stent of claim 1, wherein when the elongated tubular member is in the expanded configuration the one or more anti-migration features bend back on itself.

6. The stent of claim 1, wherein the first and second joint bends are configured to cause the anti-migration loop to lie flat as the elongated tubular body is moved from the expanded configuration to the collapsed configuration.

7. The stent of claim 1, wherein when the elongated tubular member is in the collapsed configuration at least a portion of the one or more anti-migration features is subsumed into one or more adjacent twisted knit stitches.

8. The stent of claim 1, wherein a length of the intermediate rung portions in the collapsed configuration is less than a length of the intermediate rung portions in the expanded configuration.

9. The stent of claim 1, wherein a diameter of the elongated tubular member in the collapsed configuration is in the range of about 60% to 80% less than a diameter of the elongated tubular member in the expanded configuration.

10. A stent, the stent comprising:
an elongated tubular member comprising at least one knitted filament having a plurality of twisted knit stitches each including a loop portion and an overlapping base region with intermediate rung portions extending between adjacent twisted knit stitches and at least some of the plurality of twisted knit stitches are suspended from an intermediate rung portion of a preceding row, the elongated tubular member configured to move between a collapsed configuration and an expanded configuration; and
one or more anti-migration features formed in one or more of the intermediate rung portions;
wherein when the elongated tubular member is in the expanded configuration, the one or more anti-migration features extend radially therefrom; and
wherein the one or more anti-migration features each includes a first joint bend adjacent an overlapping base region of a first twisted knit stitch and a second joint bend adjacent an overlapping base region of a second twisted knit stitch.

11. The stent of claim 10, wherein the one or more anti-migration features are positioned at a similar longitudinal location about a circumference of the elongated tubular member.

12. The stent of claim 10, wherein the one or more anti-migration features extend in the range of 1 to 4 millimeters radially beyond a base diameter of the elongated tubular member in the expanded configuration.

13. The stent of claim 10, wherein when the elongated tubular member is in the expanded configuration the one or more anti-migration features extend at a non-parallel angle relative to a longitudinal axis of the elongated tubular body.

14. The stent of claim 10, wherein when the elongated tubular member is in the expanded configuration the one or more anti-migration features bend back on itself.

15. A stent, the stent comprising:
an elongated tubular member comprising at least one knitted filament having a plurality of twisted knit stitches with intermediate rung portions extending between adjacent twisted knit stitches, the elongated tubular member configured to move between a collapsed configuration and an expanded configuration; and
one or more anti-migration features formed in one or more of the intermediate rung portions;
wherein when the elongated tubular member is in the expanded configuration, the one or more anti-migration features extend radially therefrom; and
wherein the one or more anti-migration features extend in the range of 1 to 4 millimeters radially beyond a base diameter of the elongated tubular member in the expanded configuration.

16. A stent, the stent comprising:

an elongated tubular member comprising at least one knitted filament having a plurality of twisted knit stitches with intermediate rung portions extending between adjacent twisted knit stitches, the elongated tubular member configured to move between a collapsed configuration and an expanded configuration; and one or more anti-migration features formed in one or more of the intermediate rung portions;

wherein when the elongated tubular member is in the expanded configuration, the one or more anti-migration features extend radially therefrom; and wherein when the elongated tubular member is in the expanded configuration the one or more anti-migration features bend back on itself.

17. A stent, the stent comprising:

an elongated tubular member comprising at least one knitted filament having a plurality of twisted knit stitches with intermediate rung portions extending between adjacent twisted knit stitches, the elongated tubular member configured to move between a collapsed configuration and an expanded configuration; and one or more anti-migration features formed in one or more of the intermediate rung portions;

wherein when the elongated tubular member is in the expanded configuration, the one or more anti-migration features extend radially therefrom; and wherein a diameter of the elongated tubular member in the collapsed configuration is in the range of about 60% to 80% less than a diameter of the elongated tubular member in the expanded configuration.

* * * * *